US008435557B2

(12) United States Patent
Enas et al.

(10) Patent No.: US 8,435,557 B2
(45) Date of Patent: *May 7, 2013

(54) METHOD FOR PRODUCING STERILE POLYNUCLEOTIDE BASED MEDICAMENTS

(75) Inventors: Joel Enas, Fallbrook, CA (US); Andrew Geall, Littleton, MA (US)

(73) Assignee: Vical Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/109,944

(22) Filed: Apr. 25, 2008

(65) Prior Publication Data

US 2008/0287387 A1    Nov. 20, 2008

Related U.S. Application Data

(63) Continuation of application No. 10/725,015, filed on Dec. 2, 2003, now Pat. No. 7,381, 422.

(60) Provisional application No. 60/435,303, filed on Dec. 23, 2002.

(51) Int. Cl.
  A61K 9/127    (2006.01)
  A61K 47/30    (2006.01)
  C07H 21/04    (2006.01)
  C08K 5/07     (2006.01)

(52) U.S. Cl.
  USPC ....... 424/450; 536/23.1; 514/772.3; 525/162; 977/800

(58) Field of Classification Search .................... None
See application file for complete search history.

(56) References Cited

U.S. PATENT DOCUMENTS

| 5,264,618 | A |   | 11/1993 | Felgner et al. |
| 5,459,127 | A |   | 10/1995 | Felgner et al. |
| 5,567,859 | A |   | 10/1996 | Emanuele et al. |
| 5,641,665 | A |   | 6/1997  | Hobart et al. |
| 5,656,611 | A | * | 8/1997  | Kabanov et al. ............. 514/44 A |
| 5,674,911 | A |   | 10/1997 | Emanuele et al. |
| 5,679,354 | A |   | 10/1997 | Morein et al. |
| 5,691,387 | A |   | 11/1997 | Emanuele et al. |
| 5,696,298 | A |   | 12/1997 | Emanuele et al. |
| 5,703,055 | A |   | 12/1997 | Felgner et al. |
| 5,709,879 | A |   | 1/1998  | Barchfeld et al. |
| 5,811,088 | A | * | 9/1998  | Hunter et al. ............... 424/78.08 |
| 5,817,334 | A |   | 10/1998 | Schmidt et al. |
| 5,824,322 | A |   | 10/1998 | Balasubramanian |
| 5,990,241 | A |   | 11/1999 | Emanuele et al. |
| 5,994,314 | A |   | 11/1999 | Eljamal et al. |
| 5,994,317 | A |   | 11/1999 | Wheeler |
| RE36,665  | E |   | 4/2000  | Emanuele et al. |
| 6,086,899 | A | * | 7/2000  | Balasubramanian et al. ........... 424/280.1 |
| 6,147,055 | A |   | 11/2000 | Hobart et al. |
| 6,218,112 | B1| * | 4/2001  | Thatcher et al. .................. 435/6 |
| 6,248,363 | B1|   | 6/2001  | Patel et al. |
| 6,251,599 | B1|   | 6/2001  | Chen et al. |
| 6,331,525 | B1| * | 12/2001 | Chiou et al. ................. 514/44 R |
| 6,359,054 | B1|   | 3/2002  | Lemieux et al. |
| 6,399,588 | B1|   | 6/2002  | Hobart et al. |
| 6,482,518 | B1|   | 11/2002 | Short et al. |
| 6,537,813 | B1| * | 3/2003  | Chen et al. ..................... 435/455 |
| 6,545,138 | B1|   | 4/2003  | Sugihara et al. |
| 6,586,409 | B1|   | 7/2003  | Wheeler |
| 6,670,332 | B1|   | 12/2003 | Wheeler |
| 6,747,690 | B2|   | 6/2004  | Molgaard |
| 6,867,195 | B1|   | 3/2005  | Felgner et al. |
| 6,875,748 | B2|   | 4/2005  | Manthorpe et al. |
| 6,933,286 | B2| * | 8/2005  | Emanuele et al. .......... 514/44 A |
| 7,105,574 | B1|   | 9/2006  | Wheeler |
| 7,250,404 | B2|   | 7/2007  | Felgner et al. |
| 7,381,422 | B2| * | 6/2008  | Enas et al. ..................... 424/450 |
| 7,410,795 | B2| * | 8/2008  | Hermanson et al. ....... 435/320.1 |
| 7,521,187 | B2| * | 4/2009  | Geall ................................. 435/6 |
| 2001/0007771 | A1 |  | 7/2001 | Sullivan et al. |
| 2002/0019358 | A1 |  | 2/2002 | Manthorpe et al. |
| 2002/0082237 | A1 |  | 6/2002 | Sullivan et al. |
| 2003/0032615 | A1 |  | 2/2003 | Felgner et al. |

(Continued)

FOREIGN PATENT DOCUMENTS

WO   WO 96/04392 A2   2/1996
WO   WO 96/04932 A1   2/1996

(Continued)

OTHER PUBLICATIONS

Baumgartner, I., et al., "Constitutive Expression of phVEGF165 After Intramuscular Gene Transfer Promotes Collateral Vessel Development in Patients With Critical Limb Ischemia," *Circulation* 97:1114-1123, American Heart Association, Inc. (1998).

Chen, Z.Y., et al., "Linear DNAs Concatemerize in vivo and Result in Sustained Transgene Expression in Mouse Liver," *Mol. Ther.* 3:403-410, The American Society of Gene Therapy (2001).

Cheng, S.H., and Scheule, R.K., "Airway delivery of cationic lipid: DNA complexes for cystic fibrosis," *Adv. Drug Deliv. Rev.* 30:173-184, Elsevier Science B.V. (1998).

Cherng, J.-Y., et al., "Effect of DNA topology on the transfection efficiency of poly((2-dimethylamino)ethyl methacrylate)-plasmid complexes," *J. Control. Release* 60:343-353, Elsevier Science B.V. (1999).

(Continued)

Primary Examiner — Richard Schnizer
(74) Attorney, Agent, or Firm — Sughrue Mion, PLLC

(57) ABSTRACT

The present invention relates to a novel method for producing formulations comprising a polynucleotide, block copolymer and cationic surfactant. The formulations produced by the current method are suitable for use in polynucleotide based medicaments. A suitable method of production disclosed herein additionally comprises cold filtering a mixture of a polynucleotide, block copolymer and cationic surfactant, thereby sterilizing the formulation. The method of the present invention also eliminates the need for thermal cycling of the formulation, thereby reducing the time and expense required to produce large quantities of a formulation during commercial manufacturing. The present invention also relates to novel cationic lipids.

9 Claims, 9 Drawing Sheets

U.S. PATENT DOCUMENTS

| | | |
|---|---|---|
| 2003/0049266 A1 | 3/2003 | Fearon et al. |
| 2003/0129242 A1* | 7/2003 | Bosch et al. .................. 424/489 |
| 2003/0186913 A1 | 10/2003 | Wolff et al. |
| 2003/0191082 A1 | 10/2003 | Wheeler |
| 2003/0203863 A1 | 10/2003 | Hobart et al. |
| 2004/0157789 A1 | 8/2004 | Geall |
| 2004/0162256 A1 | 8/2004 | Geall et al. |
| 2004/0171572 A1 | 9/2004 | Wheeler |
| 2004/0209241 A1 | 10/2004 | Hermanson et al. |
| 2005/0065107 A1 | 3/2005 | Hobart et al. |
| 2006/0024670 A1 | 2/2006 | Luke et al. |
| 2006/0134221 A1 | 6/2006 | Geall |
| 2007/0105193 A1 | 5/2007 | Vilalta et al. |
| 2007/0105799 A1 | 5/2007 | Hermanson |
| 2007/0286869 A1 | 12/2007 | Luke et al. |
| 2008/0057080 A1 | 3/2008 | Luke et al. |
| 2008/0085870 A1 | 4/2008 | Hermanson et al. |
| 2008/0207550 A1 | 8/2008 | Fearon et al. |

FOREIGN PATENT DOCUMENTS

| | | |
|---|---|---|
| WO | WO 96/40265 | 12/1996 |
| WO | WO 97/40839 A1 | 11/1997 |
| WO | WO 99/06055 A1 | 2/1999 |
| WO | WO 99/21591 A1 | 5/1999 |
| WO | WO 99/45966 | 9/1999 |
| WO | WO 00/57917 A2 | 10/2000 |
| WO | WO 01/36583 | 5/2001 |
| WO | WO 01/65911 A2 | 9/2001 |
| WO | WO 02/00844 * | 1/2002 |
| WO | WO 02/00844 A2 | 1/2002 |
| WO | WO 2004/060059 A2 | 7/2004 |
| WO | WO 2004/060363 A1 | 7/2004 |

OTHER PUBLICATIONS

Cherng, J.-Y., et al., "Stabilization of polymer-based gene delivery systems," *Intl. J. Pharm. 183*:25-28, Elsevier Science B.V. (1999).

Corveleyn, S, and Remon, J.P., "Maltodextrins as Lyoprotectants in the Lyophilization of a Model Protein, LDH," *Pharm. Res. 13*:146-150, Plenum Publishing Corporation (1996).

Dalesandro, J., et al., "Gene Therapy for Donor Hearts: Ex Vivo Liposome-Mediated Transfection," *J. Thorac. Cardiovasc. Surg. 111*:416-422, Mosby-Year Book, Inc. (1996).

Danko, I., et al., "Dystrophin expression improves myofiber survival in *mdx* muscle following intramuscular plasmid DNA injection," *Hum. Mol. Genet. 2*:2055-2061, Oxford University Press (1993).

Darquet, A.-M., et al., "A new DNA vehicle for nonviral gene delivery: supercoiled minicircle," *Gene Ther. 4*:1341-1349, Stockton Press (1997).

Davis, H.L., et al., "Direct gene transfer in skeletal muscle: plasmid DNA-based immunization against the hepatitis B virus surface antigen," *Vaccine 12*:1503-1509, L.R. Printing Services Ltd. (1994).

Dow, S.W., et al., "Systemic and Local Interferon γ Gene Delivery to the Lungs for Treatment of Allergen-Induced Airway Hyperresponsiveness in Mice," *Hum. Gene Ther. 10*:1905-1914, Mary Ann Liebert, Inc. (1999).

Gramzinski, R., et al., "Immune Response to a Hepatitis B DNA Vaccine in Aotus Monkeys: A Comparison of Vaccine Formulation, Route, and Method of Administration," *Mol. Med. 4*:109-118, The Picower Institute Press (1998).

Harland, R., and Misher, L., "Stability of RNA in developing Xenopus embryos and identification of a destabilizing sequence in TFIIIA messenger RNA," *Development 102*:837-852, The Company of Biologists Limited (1988).

Horton, H.M., et al., "A gene therapy for cancer using intramuscular injection of plasmid DNA encoding interferon α," *Proc. Natl. Acad. Sci. USA 96*:1553-1558, National Academy of Sciences (1999).

Kim, A.I., et al., "The Physical State of Mannitol after Freeze-Drying: Effects of Mannitol Concentration, Freezing Rate, and a Noncrystallizing Cosolute," *J. Pharm. Sci. 87*:931-935, American Chemical Society (1998).

Levy, M.Y., et al., "Characterization of plasmid DNA transfer into mouse skeletal muscle: evaluation of uptake mechanism, expression and secretion of gene products into blood," *Gene Ther. 3*:201-211, Stockton Press (1996).

Martini, A., et al., "Use of subambient differential scanning calorimetry to monitor the frozen-state behavior of blends of excipients for freeze-drying ," *PDA J. Pharm. Sci. Tech. 51*:62-67, PDA, Inc. (1997).

Martini, A., et al., "Use of subambient differential scanning calorimetry to monitor the frozen state behaviour of amino acids in simulated freeze-drying conditions," *STP Pharma. Sci. 7*:377-381, STP Pharma Sciences (1997).

Mir, L.M., et al., "High-efficiency gene transfer into skeletal muscle mediated by electric pulses," *Proc. Natl. Acad. Sci. USA 96*:4262-4267, National Academy of Sciences (1999).

Moffatt, M., and Cookson, W., "Naked DNA: New shots for allergy?," *Nat. Med. 2*:515-516, Nature America Inc. (1996).

Molina, M.C., et al., "Maintenance of nonviral vector particle size during the freezing step of the lyophilization process is insufficient for preservation of activity: insight from other structural indicators," *J. Pharma. Sci. 90*:1445-1455, Wiley-Liss, Inc. (Oct. 2001).

Newman, M.J., et al., "Use of Nonionic Block Copolymers in Vaccines and Therapeutics," *Crit. Rev. Ther. Drug Carrier Syst. 15*:89-142, Begell House, Inc. (1998).

Novo, F.J., et al., "Gene transfer and expression of human a-galactosidase from mouse muscle in vitro and in vivo," *Gene Ther. 4*:488-492, Stockton Press (1997).

Oliyai, C., et al., "Chemical Pathways of Peptide Degradation. VII. Solid State Chemical Instability of an Aspartyl Residue in a Model Hexapeptide," *Pharma. Res. 11*:901-908, Plenum Publishing Corporation (1994).

Orizio, G., et al., "Freeze-dried mannitol for injectable preparations using an automatic lyophilization cycle," *Boll. Chim. Farmaceutico 132*:368-374, Società Editoriale Farmaceutica (1993).

Österberg, T., et al., "Development of a Freeze-Dried Albumin-Free Formulation of Recombinant Factor VIII SQ," *Pharma. Res. 14*:892-898, Plenum Publishing Corporation (1997).

Pelletier, J., and Sonenberg, N., "Internal initiation of translation of eukaryotic mRNA directed by a sequence derived from poliovirus RNA," *Nature 334*:320-325, Macmillan Magazines Ltd. (1988).

Piccirillo, C.A., and Prud'Homme, G.J., "Prevention of Experimental Allergic Encephalomyelitis by Intramuscular Gene Transfer with Cytokine-Encoding Plasmid Vectors," *Hum. Gene Ther. 10*:1915-1922, Mary Ann Liebert, Inc. (1999).

Piccirillo, C.A., et al., "TGF-β1 Somatic Gene Therapy Prevents Autoimmune Disease in Nonobese Diabetic Mice," *J. Immunol. 161*:3950-3956, The American Association of Immunologists (1998).

Qin, L., et al., "Gene Transfer for Transplantation—Prolongation of Allograft Survival with Transforming Growth Factor-β1," *Ann. Surg. 220*:508-519, J.B. Lippincott Company (1994).

Qin, Y.-J., et al., "Gene Suture—A Novel Method for Intramuscular Gene Transfer and its Application in Hypertension Therapy," *Life Sci. 65*:2193-2203, Elsevier Science Inc. (1999).

Ragno, S., et al., "Protection of Rats from Adjuvant Arthritis by Immunization with Naked DNA Encoding for Mycobacterial Heat Shock Protein 65," *Arthritis Rheum. 40*:277-283, American College of Rheumatology (1997).

Restifo, N.P., et al., "Enhancing the Recognition of Tumour Associated Antigens," *Folia Biologica 40*:74-88, Institute of Molecular Genetics (1994).

Schrijver, R.S., et al., "Immunization of cattle with a BHV1 vector vaccine or a DNA vaccine both coding for the G protein of BRSV," *Vaccine 15*:1908-1916, Elsevier Science Ltd. (1997).

Todd, C.W., et al., "Development of an adjuvant-active nonionic block copolymer for use in oil-free subunit vaccines formulations," *Vaccine 15*:564-570, Elsevier Science Ltd. (1997).

Todd, C.W., et al., "Systematic Development of a Block Copolymer Adjuvant for Trivalent Influenza Virus Vaccine," *Dev. Biol. Stand. 92*:341-351, Karger (1998).

Tripathy, S.K., et al., "Long-term expression of erythropoietin in the systemic circulation of mice after intramuscular injection of a plasmid DNA vector," *Proc. Natl. Acad. Sci. USA 93*:10876-10880, National Academy of Sciences (1996).

Tse, C., and Capeau, J., "Quantification des acides nucléiques par PCR quantitative en temps réel," *Ann. Biol. Clin. 61*:279-293, John Libbet Eurotext (May-Jun. 2003).

Tsurumi, Y., et al., "Direct Intramuscular Gene Transfer of Naked DNA Encoding Vascular Endothelial Growth Factor Augments Collateral Development and Tissue Perfusion," *Circulation 94*:3281-3290, American Heart Association, Inc. (1996).

Ulmer, J.B., et al., "Immunization against Viral Proteins with Naked DNA," *Ann. N.Y. Acad. Sci. 772*:117-125, New York Academy of Sciences (1995).

Vahlsing, H.L., et al., "Immunization with plasmid DNA using a pneumatic gun," *J. Immunol. Methods 175*:11-22, Elsevier Science B.V. (1994).

Wade, A., and Weller, P.J., eds., "Benzalkonium Chloride," "Benzethonium Chloride," "Cetrimide," in: *Handbook of Pharmaceutical Excipients*, American Pharmaceutical Association, Washington, DC, pp. 27-31, 96-98 (1994).

Yagi, K., et al., "Basic Study on Gene Therapy of Human Malignant Glioma by Use of the Cationic Multilamellar Liposome-Entrapped Human Interferon β Gene," *Hum. Gene Ther. 10*:1975-1982, Mary Ann Liebert, Inc. (1999).

Co-Pending U.S. Appl. No. 09/478,457, Wolff, et al., filed Jan. 6, 2000 (Not Published).

Co-pending U.S. Appl. No. 11/889,977, Wheeler, C.J., filed Aug. 17, 2007 (Not Published).

Co-pending U.S. Appl. No. 11/889,980, Wheeler, C.J., filed Aug. 17, 2007 (Not Published).

Co-pending U.S. Appl. No. 11/892,035, Hermanson, et al., filed Aug. 17, 2007 (Not Published).

Co-pending U.S. Appl. No. 11/892,016, Luke, et al., filed Aug. 17, 2007 (Not Published).

Tripathy, et al. "Long-term expression of erythropoitin in the systemic circulation of mice after intramuscular injection of a plasmid DNA vector", Proc. Natl. Acad. Sci. USA, 93:10876-10880, national academy of sciences (1996).

\* cited by examiner

METHOD FOR PRODUCING STERILE POLYNUCLEOTIDE BASED MEDICAMENTS

CROSS-REFERENCE TO RELATED APPLICATIONS

The present application is a continuation of U.S. application Ser. No. 10/725,015, filed Dec. 2, 2003, now allowed, which claims the benefit of the filing date of U.S. Provisional Application No. 60/435,303 filed Dec. 23, 2002, which is incorporated herein by reference in its entirety.

BACKGROUND OF THE INVENTION

1. Field of the Invention

The present invention relates to a novel method for producing formulations comprising a polynucleotide, a block copolymer and cationic surfactant. The formulations produced by the current method are suitable for use in polynucleotide based medicaments.

2. Related Art

The use of non-ionic block copolymers as adjuvants in gene and vaccine delivery has been documented in the art. Newman et al. (*Critical Reviews in Therapeutic Drug Carrier Systems* 15 (2): 89-142 (1998)) review a class of non-ionic block copolymers which show adjuvant activity. The basic structure comprises blocks of polyoxyethylene (POE) and polyoxypropylene (POP) such as a POE-POP-POE block copolymer. Newman et al. id., disclose that certain POE-POP-POE block copolymers may be useful as adjuvants to an influenza protein-based vaccine, namely higher molecular weight POE-POP-POE block copolymers containing a central POP block having a molecular weight of over about 9000 daltons to about 20,000 daltons and flanking POE blocks which comprise up to about 20% of the total molecular weight of the copolymer (See U.S. Reissue Pat. No. 36,665, U.S. Pat. No. 5,567,859, U.S. Pat. No. 5,691,387, U.S. Pat. No. 5,696, 298 and U.S. Pat. No. 5,990,241, all issued to Emanuele, et al., regarding these POE-POP-POE block copolymers). Published International Patent Application No. WO 96/04932 further discloses higher molecular weight POE/POP block copolymers which have surfactant characteristics and show biological efficacy as vaccine adjuvants.

U.S. Pat. No. 5,656,611 and Published International Patent Application No. WO 99/06055 disclose compositions which include a polynucleotide, and a block copolymer containing a non-ionic portion and a polycationic portion. A surfactant is added to increase solubility and the end result is the formation of micelles. This formulation allows stabilization of polynucleic acids and enhances transfection efficiency. Published International Patent Application No. WO 99/21591 discloses a soluble ionic complex comprising an aqueous mixture of a polynucleotide and a benzylammonium group-containing cationic surfactant and the use of this complex in vaccine and gene delivery.

Recent disclosure in Published International Patent Application No. WO 02/00844, hereby incorporated in its entirety by reference, describes polynucleotide vaccine adjuvants which comprise a polynucleotide, a block copolymer and a cationic surfactant. By including the cationic surfactant in the formulation, the percentage of polynucleotide that is associated with the block copolymer/cationic surfactant adjuvant is increased. In addition, this formulation has demonstrated enhanced in vivo immune response to polynucleotide vaccines and/or gene therapy-based transgenes.

However, the method described in Published International Patent Application No. WO 02/00844 to produce this polynucleotide/block copolymer/cationic surfactant composition requires thermally cycling the mixture several times through the cloud point of the block copolymer to form the polynucleotide complexes. These multiple heating and cooling cycles are expensive and time consuming, especially when considering the production of large quantities of the formulation required during commercial manufacturing. In addition, no sterilization step was disclosed in WO 02/00844. The requirement to sterilize all components prior to mixing and producing the formulation under sterile conditions increases the cost of large-scale production considerably and hinders the ability to scale up the production of this formulation for commercial manufacturing.

Therefore, a need remains in the art for a method of producing sterile formulations as described above, that also allow for a scalable production platform.

BRIEF SUMMARY OF THE INVENTION

The present invention addresses and meets the needs in the art by providing (1) a cold filtration process which sterilizes the formulation and (2) a method of production whereby the solution does not need to by cycled through the cloud point. This method results in complexes with particle size and surface charge (zeta potential) similar to formulations described previously.

The present intentional also describes the use of several novel cationic lipids for use in the methods of the invention: (±)-N-(Benzyl)-N,N-dimethyl-2,3-bis(hexyloxy)-1-propanaminium bromide (Bn-DHxRIE), (±)-N-(2-Acetoxyethyl)-N,N-dimethyl-2,3-bis(hexyloxy)-1-propanaminium bromide (DHxRIE-OAc), (±)-N-(2-Benzoyloxyethyl)-N,N-dimethyl-2,3-bis(hexyloxy)-1-propanaminium bromide (DHxRIE-OBz), (±)-N-(3-Acetoxypropyl)-N,N-dimethyl-2, 3-bis(octyloxy)-1-propanaminium chloride (Pr-DOctRIE-OAc).

The present invention relates to a novel method for producing a polynucleotide formulation suitable for use in polynucleotide based medicaments. In particular, the method comprises (a) mixing: (i) a cationic surfactant; (ii) a block copolymer and (iii) a population of polynucleotide molecules; at a temperature below the cloud point of said block copolymer to form a mixture; and (b) cold filtering the mixture to produce a sterile formulation.

In certain embodiments, the method can further comprise raising the temperature of the mixture above the cloud point of said block copolymer before or after step (b). Furthermore, the method can comprise cycling the mixture between temperatures above and below the cloud point of said block copolymer for multiple cycles.

Useful cationic surfactants of the present invention include benzalkonium chloride (BAK) and Pr-DOctRIE-OAc. The invention relates to a method comprising non-ionic block copolymers such as the polyoxyethylene (POE)/polyoxypropylene (POP) types. Specifically, block co-polymers such as Poloxamer CRL-1005.

The method of the present invention relates to the production of a sterile formulation comprising a block copolymer which forms microparticles, ranging in size from about 100 nm to about 2000 nm, has a cloud point between about 1° C. to about 20° C. and associates with a cationic surfactant which may associate with the block copolymer and nucleic acid molecules to form a microparticle.

The current invention provides improved methods for producing polynucleotide based medicaments, as described in more detail herein. Specifically, the methods of the current invention are easily scalable for commercial production and provide a cost-effective, two-step method for producing sterile polynucleotide based medicaments.

The current invention is also directed to a cationic lipid selected from the group consisting of: Bn-DHxRIE, DHxRIE-OAc, DHxRIE-OBz and Pr-DOctRIE-OAc.

BRIEF DESCRIPTION OF THE DRAWINGS/FIGURES

Figure 7:
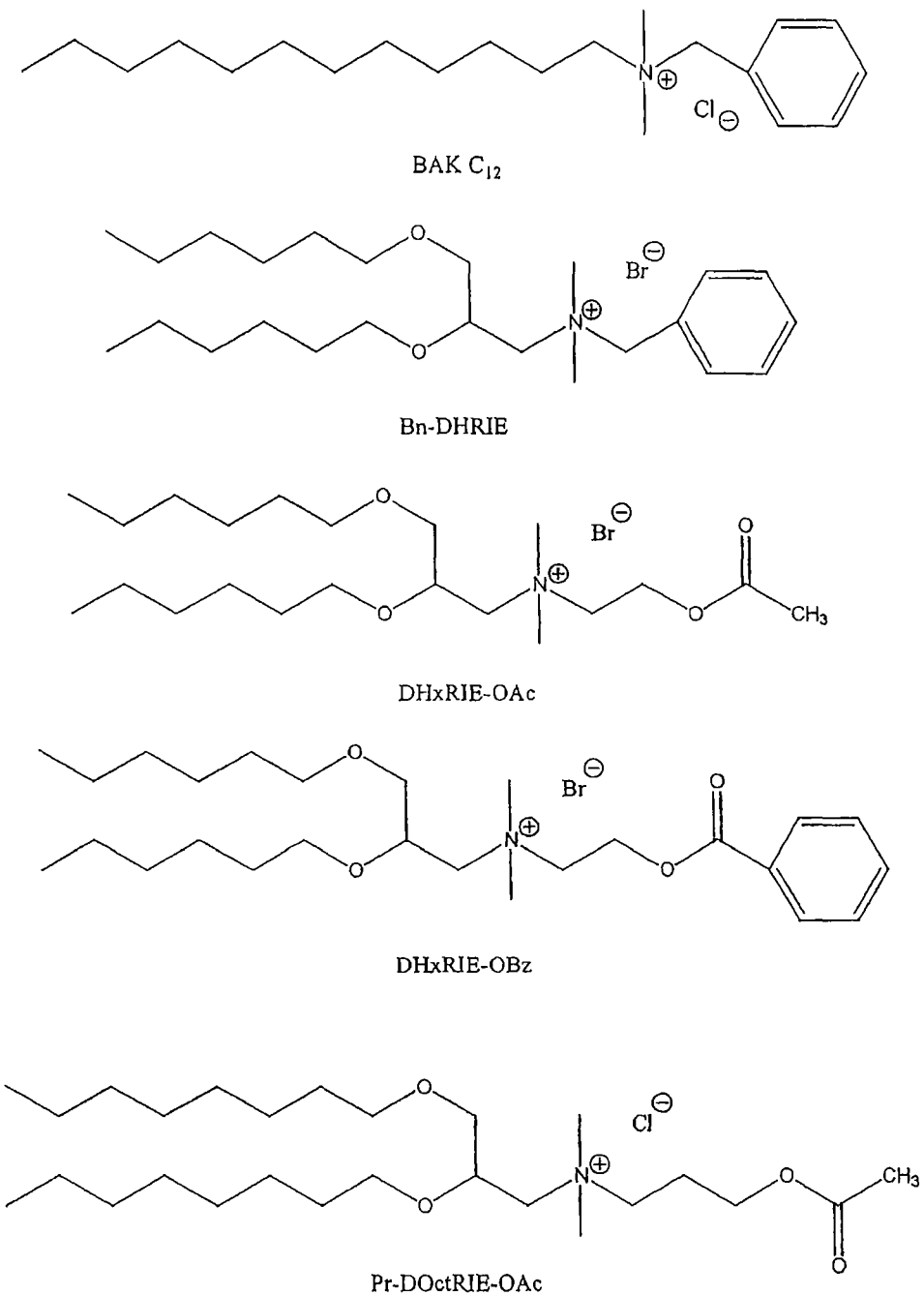

FIG. 7 contains the structures of the following cationic lipids: BAK C12, Bn-DHxRIE, DHxRIE-OAc, DHxRIE-OBz and Pr-DOctRIE-OAc.

DETAILED DESCRIPTION OF THE INVENTION

As used herein, "PBS" refers to—phosphate buffered saline—.

As used herein, "BAK" refers to—benzalkonium chloride—.

As used herein, "BEC" refers to—benzethonium chloride—.

As used herein, "CPC" refers to—cetylpyridinium chloride—.

As used herein, "CTAC" refers to—cetyl trimethylammonium chloride—.

As used herein, "PS-80" refers to—polysorbate 80—.

As used herein, "mixture" and "solution" are interchangeable.

As used herein, the words "particle" and "microparticle" are interchangeable.

As used herein, the term "cloud point" refers to the point in a temperature shift, or other titration, at which a clear solution becomes cloudy, i.e., when a component dissolved in a solution begins to precipitate out of solution.

As used herein, the term "adjuvant" is any substance or combination of substances which nonspecifically enhances the immune response to an antigen; and also relates to any substance which enhances the immune response directly related to delivery of a polynucleotide within a vertebrate or mammalian host, such as a human or non-human mammalian host, such that administration of the adjuvant in combination with the polynucleotide results in an increased in vivo immune response to expression of the intended antigen or antigens encoded by the polynucleotide. Included in this definition are substances which may act as facilitators of gene delivery, thereby increasing the amount of plasmid DNA delivered to cells that can express the intended antigen. Substances which may enhance delivery of plasmid DNA would include those which do not substantially interact with the plasmid DNA in the formulation and substances which do interact with the plasmid DNA, forming tightly bound or weakly bound complexes between the adjuvant and the plasmid DNA, either in vitro or in vivo.

As used herein, the term "polynucleotide" is a nucleic acid molecule which contains essential regulatory elements such that upon introduction into a living, vertebrate cell, the nucleic acid molecule is able to direct the cellular machinery to produce translation products encoded by the genes comprising the nucleic acid molecule.

As used herein, the term "polynucleotide based medicament" is used to indicate polynucleotide based compositions, including compositions which comprise the block copolymers and cationic surfactants disclosed herein, useful for a vehicle to deliver a transgene of interest to a vertebrate host, such as a human or non-human mammalian host, or to provide or promote detectable and/or therapeutic levels of expression of the transgene, and/or to generate or promote an immune response to the expression product of the transgene.

As used herein, the term "vector" refers to a vehicle by which DNA fragments, most likely comprising a transgene or portion thereof which expresses an antigen or antigenic epitope, can be introduced into a host organism or host tissue. There are various types of vectors which include but are not limited to recombinant vectors, including DNA plasmid vectors, recombinant viral vectors such as adenovirus vectors, retrovirus vectors and adeno-associated virus vectors, as well as bacteriophage vectors and cosmid vectors.

The term "gene" or "transgene" refers to a segment of nucleic acid molecule which encodes a discrete protein or a portion thereof, such as a portion of the full-length protein which will induce an appropriate immune response within the host.

The present invention relates to a novel method for producing a sterile formulation suitable for use in polynucleotide based medicaments. The method results in a sterile formulation comprising a population of polynucleotide molecules, a block copolymer, and a cationic surfactant. The method of the present invention is an improvement of previously described methods as it includes just two-steps which is easier and more cost-effective to produce on a commercial scale.

The method of the present invention comprises mixing:
(i) a cationic surfactant;
(ii) a block copolymer; and
(iii) a polynucleotide;
at a temperature below the cloud point of said block copolymer to form a mixture. Suitable components of the present invention are described herein.

The order in which components of the mixture are added may vary. A suitable order in which ingredients of the mixture may be added include, but is not limited to: (1) polynucleotide; (2) block copolymer; and (3) cationic surfactant. Alternatively, the order of addition can also include: (1) cationic surfactant; (2) block copolymer; and (3) polynucleotide. Stirring of the mixture can occur once all components have been added, concurrently while components are being added, or in between the addition of components.

The block copolymers useful in the polynucleotide based medicament formulations described herein are block copolymers which form microparticles at room temperature (above the block copolymer cloud point) and may associate with a population of nucleic acid molecules, such as a population of plasmid DNA molecules, with and without the addition of cationic surfactants. The nucleic acid molecule of the present invention may include a deoxyribonucleic acid molecule (DNA), such as genomic DNA and complementary DNA (cDNA) as well as a ribonucleic acid molecule (RNA). In regard to the block copolymer, a suitable group of copolymers used in the methods of the present invention include non-ionic block copolymers which comprise blocks of polyoxyethylene (POE) and polyoxypropylene (POP).

The present invention relates to a method for producing a sterile formulation suitable for use in polynucleotide based medicaments which comprise in part a non-ionic block copolymer. While the invention contemplates use of any such block copolymer which promotes generation of a particle size and surface charge as described herein, a suitable non-ionic block copolymer is a polyoxyethylene (POE)/polyoxypropylene (POP) block copolymer, especially a higher molecular weight POE-POP-POE block copolymer. These compounds are described in U.S. Reissue Pat. No. 36,665, U.S. Pat. No. 5,567,859, U.S. Pat. No. 5,691,387, U.S. Pat. No. 5,696,298 and U.S. Pat. No. 5,990,241, and WO 96/04392, all of which are hereby incorporated by reference.

Briefly, these non-ionic block copolymers have the following general formula: $HO(C_2H_4O)_x(C_3H_6O)_y(C_2H_4O)_xH$ wherein (y) represents a number such that the molecular weight of the hydrophobic POP portion $(C_3H_6O)$ is up to approximately 20,000 daltons and wherein (x) represents a number such that the percentage of hydrophilic POE portion $(C_2H_4O)$ is between approximately 1% and 50% by weight.

A suitable POE-POP-POE block copolymer that can be used in the methods of the present invention has the following formula $HO(C_2H_4O)_x(C_3H_6O)_y(C_2H_4O)_xH$ wherein (y) represents a number such that the molecular weight of the hydrophobe $(C_3H_6O)$ is between approximately 9000 Daltons and 15,000 Daltons and (x) represents a number such that the percentage of hydrophile $(C_2H_4O)$ is between approximately 3% and 35%.

An alternative POE-POP-POE block copolymer that can be used in the method of the present invention has the following formula $HO(C_2H_4O)_x(C_3H_6O)_y(C_2H_4O)_xH$ wherein (y) represents a number such that the molecular weight of the hydrophobe $(C_3H_6O)$ is between approximately 9000 Daltons and 15,000 Daltons and (x) represents a number such that the percentage of hydrophile $(C_2H_4O)$ is between approximately 3% and 10%.

Yet another suitable surface-active copolymer that can be used in the method of the present invention has the following formula: $HO(C_2H_4O)_x(C_3H_6O)_y(C_2H_4O)_xH$ wherein (y) represents a number such that the molecular weight of the hydrophobe $(C_3H_6O)$ is approximately 9000 Daltons and (x) represents a number such that the percentage of hydrophile $(C_2H_4O)$ is approximately 3-5%.

Another alternative surface-active copolymer that can be used in the method of the present invention has the following formula: $HO(C_2H_4O)_x(C_3H_6O)_y(C_2H_4O)_xH$ wherein (y) represents a number such that the molecular weight of the hydrophobe $(C_3H_6O)$ is approximately 9000 Daltons and (x) represents a number such that the percentage of hydrophile $(C_2H_4O)$ is approximately 3%.

A suitable surface-active copolymer that can be used in the method of the present invention is CRL-1005. CRL-1005 has the following formula: $HO(C_2H_4O)_x(C_3H_6O)_y(C_2H_4O)_xH$ wherein (y) represents a number such that the molecular weight of the hydrophobe $(C_3H_6O)$ is approximately 12000 Daltons and (x) represents a number such that the percentage of hydrophile $(C_2H_4O)$ is approximately 5%, wherein (x) is about 7, ±1 and (y) is approximately 12,000 Daltons, with about 207 units, ±7.

A typical POE/POP block copolymer utilized herein will comprise the structure of POE-POP-POE, as reviewed in Newman et al. (*Critical Reviews in Therapeutic Drug Carrier Systems* 15 (2): 89-142 (1998)). A suitable block copolymer for use in the methods of the present invention is a POE-POP-POE block copolymer with a central POP block having a molecular weight in a range from about 1000 daltons up to approximately 20,000 daltons and flanking POE blocks which comprise up to about 50% of the total molecular weight of the copolymer. Block copolymers such as these, which are much larger than earlier disclosed Pluronic-based POE/POP block copolymers, are described in detail in U.S. Reissue Pat. No. 36,655. A representative POE-POP-POE block copolymer utilized to exemplify polynucleotide based formulations of the present invention is disclosed in Published International Patent Application No. WO 96/04392, is also described at length in Newman et al. (Id.), and is referred to as CRL-1005 (CytRx Corp).

Another suitable group of block copolymers for use in the present invention are "reverse" block copolymers wherein the hydrophobic portions of the molecule $(C_3H_6O)$ and the hydrophilic portions $(C_2H_4O)$ have been reversed such that the polymer has the formula: $HO(C_3H_6O)_y(C_2H_4O)_x(C_3H_6O)_yH$ wherein (y) represents a number such that the molecular weight of the hydrophobic POP portion $(C_3H_6O)$ is up to approximately 20,000 daltons and wherein (x) represents a number such that the percentage of hydrophilic POE portion $(C_2H_4O)$ is between approximately 1% and 50% by weight. These "reverse" block copolymers have the structure POP-POE-POP and are described in U.S. Pat. Nos. 5,656,611 and 6,359,054.

A suitable POP-POE-POP block copolymer that can be used in the invention has the following formula: $HO(C_3H_6O)_y(C_2H_4O)_x(C_3H_6O)_yH$ wherein (y) represents a number such that the molecular weight of the hydrophobe $(C_3H_6O)$ is between approximately 9000 Daltons and 15,000 Daltons and (x) represents a number such that the percentage of hydrophile $(C_2H_4O)$ is between approximately 3% and 35%.

Another suitable POP-POE-POP block copolymer that can be used in the invention has the following formula: $HO(C_3H_6O)_y(C_2H_4O)_x(C_3H_6O)_yH$ wherein (y) represents a number such that the molecular weight of the hydrophobe $(C_3H_6O)$ is between approximately 9000 Daltons and 15,000 Daltons and (x) represents a number such that the percentage of hydrophile $(C_2H_4O)$ is between approximately 3% and 10%.

Another suitable surface-active copolymer that can be used in the invention and has the following formula: $HO(C_3H_6O)_y(C_2H_4O)_x(C_3H_6O)_yH$ wherein (y) represents a number such that the molecular weight of the hydrophobe $(C_3H_6O)$ is approximately 12000 Daltons and (x) represents a number such that the percentage of hydrophile $(C_2H_4O)$ is approximately 5%.

An alternative surface-active copolymer that can be used in the invention has the following formula: $HO(C_3H_6O)_y(C_2H_4O)_x(C_3H_6O)_yH$ wherein (y) represents a number such that the molecular weight of the hydrophobe ($C_3H_6O$) is approximately 9000 Daltons and (x) represents a number such that the percentage of hydrophile ($C_2H_4O$) is approximately 3-5%.

Another suitable surface-active copolymer that can be used in the invention has the following formula: $HO(C_3H_6O)_y(C_2H_4O)_x(C_3H_6O)_yH$ wherein (y) represents a number such that the molecular weight of the hydrophobe ($C_3H_6O$) is approximately 9000 Daltons and (x) represents a number such that the percentage of hydrophile ($C_2H_4O$) is approximately 3%.

The block copolymers of the present invention are amphipathic compounds with inverse solubility characteristics in aqueous media. Below their cloud points (1-20° C.) these copolymers are water-soluble and form clear solutions that can be filter sterilized. The solution process involves the formation of hydrogen bonds between oxygen atoms and hydroxyl groups in the copolymer and water molecules. When a solution of copolymer is warmed and passes through its cloud point, the increased thermal motion is sufficient to break the hydrogen bonds and as the copolymer comes out of solution, they self-assemble into microparticles (Todd, C. W., Pozzi, L.-A. M., Guarnaccia, J. R., Balusubramanian, M., Henk, W. G., Younger, L. E., and Newman, M. J. *Vaccine* 15, 564-570 (1997) and Todd, C. W., Lee, E., Balusubramanian, M., Shah, H., Henk, W. G., Younger, L. E., and Newman, M. J. In "Modulation of the immune response to vaccine antigens" (Brown, F., And Haaheim, L. R., Eds.) *Dev. Biol. Stand.* 92, 343-353. Karger, Basel (1997)). The process is reversible.

Although there is evidence to suggest that the association of plasmid DNA to the CRL-1005 particles leads to an improved immune response, the mechanism by which the immune response is enhanced is at present unclear. While not being bound by theory in any way, it is possible that DNA associated to CRL-1005 particles may be more readily taken up and expressed by cells. It is also possible that the negative surface charge of the CRL-1005 particles, produced by the association of plasmid DNA to CRL-1005/BAK particles, may be important for enhancing the adjuvant properties of CRL-1005. The current invention does not distinguish between these two possible mechanisms of enhancing the immune response.

One model for the interaction of plasmid DNA/the block copolymer (CRL-1005) and the cationic surfactant (for example, BAK) suggests that BAK binding to particles of CRL-1005, through hydrophobic interactions, results in a reduction of the CRL-1005 particle size and in the formation of positively charged CRL-1005 particles. Binding of the polynucleotide (plasmid DNA) is believed to occur through electrostatic interactions between the positively charged headgroup of the cationic surfactant (BAK) and the DNA phosphate groups, while the hydrophobic tail of the cationic surfactant is embedded within the block copolymer (CRL-1005) particle.

Published International Patent Application No. WO 02/00844 discloses that the generation of physically distinct particles comprising the block co-polymer CRL-1005, a cationic surfactant and DNA, further promotes the association of plasmid DNA to the block copolymer as compared to the block co-polymer and DNA alone. The particles containing all three components also resulted in a marked enhancement of a cellular immune response.

Published International Patent Application No. WO 02/00844 discloses a method for producing the particles described above. However, the method described in WO 02/00844, requires vortexing of all components and multiple cycles of cooling and heating to achieved a particle size in the range of 200-500 nm. The process of multiple heating and cooling can be quite expensive and time consuming when producing large quantities of a formulation during commercial manufacturing. The method of the present invention comprises mixing of the cationic surfactant, a block copolymer and DNA in a buffer such as PBS at a temperature below the cloud point of said block copolymer. There is no requirement for raising the mixture to a temperature above the cloud point or multiple heating and cooling steps. As FIGS. 2A and 2B demonstrate, this method results in particle sizes and polydispersity similar to the methods described previously.

Furthermore, the method of the present invention provides for a cold filtering step after mixing which results in a sterile formulation which can be used for polynucleotide based medicaments in patients. The addition of the cold filtration step allows for large scale commercial production in aseptic conditions, using aseptic components, which greatly reduces the cost of production and facilitates manufacturing.

The present invention relates to a method for producing a sterile formulation suitable for use in a polynucleotide medicaments with ease in commercial large-scale manufacturing. The method results in the generation of microparticles (at temperatures above the cloud point of CRL-1005, or another representative block copolymer) which comprise a block copolymer, cationic and polynucleotide molecules. The components which will eventually comprise the microparticles are mixed in a buffered solution, such as PBS, by stirring at temperature below the cloud point of the block copolymer. This solution is then cold filtered and optionally aliquoted into sterile vials and stored at a temperature of −80° C. Prior to administration to a patient by injection, or any other means, the vial is brought to room temperature or to a temperature above the cloud point of the block copolymer, wherein microparticle formation will occur during the warming process. It has been unexpectedly determined that microparticle formation (or warming the mixture containing the block copolymer, cationic surfactant and a polynucleotide to a temperature above the cloud point of the block copolymer) does not need to occur prior to sterilization or storage at −80° C. to produce microparticles having a diameter from about 200 nm to about 600 nm with a slightly positive zeta potential measurement in the presence of BAK but without addition of the polynucleotide (about 2.5 mV for CRL-1005 and 0.71 mM BAK) and a negative zeta potential when the polynucleotide (at 5 mg/mL) is present (about −46.6 mV for CRL-1005 and 0.71 mM BAK and 5 mg/mL plasmid DNA) as described in Published International Patent Application No. WO 02/00844. Furthermore, the inventors have also discovered that there is no need to perform heating and cooling cycles to obtain microparticles with the characteristics described above and in Published International Patent Application No. WO 02/00844.

The artisan will be able to mix and match various block copolymers, cationic surfactants, excipients, as well as utilize various concentrations of these components. The artisan will be able to measure in vitro structural characteristics of any polynucleotide based medicaments produced by the methods of the current invention as shown herein.

In a specific embodiment of the present invention polynucleotides are mixed with the poloxamer CRL-1005 and BAK (Benzalkonium chloride 50% solution, available from Ruger Chemical Co. Inc.). Specific final concentrations of each component of the formulae are described in the specific examples, but for any of these methods, the concentrations of each component may be varied by basic stoichiometric calculations known by those of ordinary skill in the art to make a final solution having the desired concentrations.

In the method of the current invention, the concentration of the block copolymer is adjusted depending on, for example, transfection efficiency, expression efficiency, or immunogenicity. In one useful embodiment, the final concentration of the block copolymer is between about 1 mg/mL to about 75 mg/mL, for example, about 3 mg/mL to about 50 mg/mL, about 5 mg/mL to about 40 mg/mL, about 6 mg/mL to about 30 mg/mL, about 6 mg/mL, about 6.5 mg/mL, about 7 mg/mL, about 7.5 mg/mL, about 8 mg/mL, about 9 mg/mL, about 10 mg/mL, about 15 mg/mL, about 20 mg/mL, about 25 mg/mL, about 30 mg/mL of block copolymer.

In the method of the current invention, the concentration of the poloxamer is adjusted depending on, for example, transfection efficiency, expression efficiency, or immunogenicity. In one useful embodiment, the final concentration of the poloxamer CRL-1005 is between about 1 mg/mL to about 75 mg/mL, for example, about 3 mg/mL to about 50 mg/mL, about 5 mg/mL to about 40 mg/mL, about 6 mg/mL to about 30 mg/mL, about 6 mg/mL, about 6.5 mg/mL, about 7 mg/mL, about 7.5 mg/mL, about 8 mg/mL, about 9 mg/mL, about 10 mg/mL, about 15 mg/mL, about 20 mg/mL, about 25 mg/mL, about 30 mg/mL of CRL-1005.

Similarly the concentration of DNA in the methods of the current invention is adjusted depending on many factors, including the amount of a formulation to be delivered, the age and weight of the subject, the delivery method and route of the polynucleotide being delivered. In a suitable embodiment, the final concentration of DNA is from about 1 ng/mL to about 30 mg/mL of plasmid (or other polynucleotide). For example, a formulation of the present invention may have a final concentration of about 0.1 mg/mL to about 20 mg/mL, about 1 mg/mL to about 10 mg/mL, about 1 mg/mL, about 2 mg/mL, about 2.5, about 3 mg/mL, about 3.5, about 4 mg/mL, about 4.5, about 5 mg/mL, about 5.5 mg/mL, about 6 mg/mL, about 7 mg/mL, about 8 mg/mL, about 9 mg/mL, about 10 mg/mL, about 20 mg/mL, or about 30 mg/mL of a plasmid (or any other polynucleotide).

Any type of polynucleotide can be incorporated into the method of the current invention. For example plasmid DNA, genomic DNA, cDNA, DNA fragments and RNA. Certain formulations of the present invention include a cocktail of plasmids. Various plasmids desired in a cocktail are combined together in PBS or other diluent prior to the addition to the other ingredients. There is no upper limit to the number of different types of plasmids which can be used in the method of the present invention. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportion, or 2, 3, 4, 5, 6, 7, 8, 9, 10 or more times as much of one plasmid may be included relative to other plasmids in the cocktail.

The polynucleotide formulations produced by the methods of the present invention also comprise a cationic surfactant. It will be known to one of skill in the art that numerous cationic surfactants may be a candidate for use in these formulations. Therefore, the invention contemplates use of any cationic surfactant which, along with a block copolymer, and a polynucleotide promotes generation of a particle size and surface charge as described herein. Cationic surfactants which can be used include, but are not limited to, benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC) and cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy) ethyl]-benzenemethanaminium chloride (DEBDA), dialkyldimethylammonium salts, -[1-(2,3-dioleyloxy)-propyl]-N,N,N,trimethylammonium chloride, 1,2-diacyl-3-(trimethylammonio) propane (acyl group=dimyristoyl, dipalmitoyl, distearoyl dioleoyl), 1,2-diacyl-3(dimethylammonio) propane (acyl group=dimyristoyl, dipalmitoyl, distearoyl, dioleoyl), 1,2-dioleoyl-3-(4'-trimethyl-ammonio)butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-a dioleoyl phosphatidylethanolamine), cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($Cl_2GluPhCnN^+$), ditetradecyl glutamate ester with pendant amino group ($Cl_4GluCnN^+$), cationic derivatives of cholesterol, including but not limited to cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3 β-carboxyamidoethylenedimethylamine, and 3β-[N-(N',N'-dimethylaminoetanecarbomoyl]cholesterol) (DC-Chol).

Other examples of cationic surfactants for use in the invention are selected from the group of cationic lipids including N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino)propyl-ammonium bromide (PA-TELO), and $N^1$-(3-aminopropyl)((2-dodecyloxy)ethyl)-$N^2$-(2-dodecyloxy) ethyl-1-piperazin aminium bromide (GA-LOE-BP), DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether).

Additional specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis (syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Other cationic lipids for use in the present invention include the compounds described in U.S. Pat. Nos. 5,264,618, 5,459,127 and 5,994,317. Non-limiting examples of these cationic lipids include (±)-N,N-dimethyl-N-[2-(sperminecarboxamido)ethyl]-2,3-bis(dioleyloxy)-1-propanaminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE), and (±)-N-(3-aminopropyl)-N,N-dimethyl-2,3-bis (dodecyloxy)-1-propaniminium bromide (GAP-DLRIE).

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(4-aminobutyl)-N,N-dimethyl-2,3-(bis-decyloxy)-1-propanaminium bromide (DAB-DDRIE), (±)-N-(3-aminopropyl)-N,N-dimethyl-2,3-(bis-tetradecyloxy)-1-propanaminium bromide (GAP-DMRIE), (±)-N-((N''-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

In a suitable aspect of the present invention, the cationic surfactant is selected from the group consisting of benzalkonium chloride, benzethonium chloride, cetramide, cetylpyridinium chloride and cetyl trimethylammonium chloride. Benzalkonium chloride is available commercially and is known to exist as a mixture of alkylbenzyldimethylammonium chlorides of the general formula: $[C_6H_5CH_2N(CH_3)2R]Cl$, where R represents a mixture of alkyls, including all or some of the group beginning with n-$C_8H_{17}$ through n-$C_{16}H_{33}$. The average MW of BAK is 360 (*Handbook of Pharmaceutical Excipients*, Ed. Wade and Weller, 1994, 2nd Ed. at page 27-29). Benzethonium chloride is N,N-dimethyl-N-[2-[2-[4-(1,1,3,3 tetramethylbutyl)phenoxy]ethoxy]ethyl]benzenemethanaminium chloride ($C_{27}H_{42}ClNO_2$), which has a molecular weight of 448.10 (*Handbook of Pharmaceutical Excipients* at page 30-31). Cetramide consists mainly of trimethyltetradecylammonium bromide ($C_{17}H_{38}BrN$), which may contain smaller amounts of dodecyltrimethyl-ammonium bromide ($C_{15}H_{34}BrN$) and hexadecyltrimethylammonium bromide ($C_{19}H_{42}BrN$), and has a molecular weight of 336.40 (*Handbook of pharmaceutical Excipients* at page 96-98).

Example of useful cationic lipids of the present invention include (±)-N-(Benzyl)-N,N-dimethyl-2,3-bis(hexyloxy)-1-propanaminium bromide (Bn-DHxRIE), (±)-N-(2-Acetoxyethyl)-N,N-dimethyl-2,3-bis(hexyloxy)-1-propanaminium bromide (DHxRIE-OAc), (±)-N-(2-Benzoyloxyethyl)-N,N-dimethyl-2,3-bis(hexyloxy)-1-propanaminium bromide (DHxRIE-OBz), (±)-N-(3-Acetoxypropyl)-N,N-dimethyl-2,3-bis(octyloxy)-1-propanaminium chloride (Pr-DOctRIE-OAc). The structures of these compounds are given in FIG. 7. These lipids have the general structure described in U.S. Pat. Nos. 5,264,618 and 5,459,127.

The lipids of and useful in the present invention have been developed using the methods and preparation protocol outlined in U.S. Pat. Nos. 5,264,618 and 5,459,127 (these methods of production are hereby incorporated by reference). The modifications made to the hydrophilic portion of the molecules make them especially suitable for use in transfection formulations and in the polynucleotide/block copolymer/cationic surfactant formulation of the present invention. In an alternative aspect of the present invention then, the cationic surfactant for use in the methods of the current invention is selected from the group consisting of Bn-DHxRIE, DHxRIE-OAc, DHxRIE-OBz and Pr-DOctRIE-OAc. In yet another aspect of the present invention, the cationic surfactant is Pr-DOctRIE-OAc.

The concentration of the cationic lipid may be adjusted depending on, for example, a desired particle size and improved stability. Indeed, in certain embodiments, the methods of the present invention include a block copolymer and DNA but are free of any cationic lipid. In general cationic lipid-containing formulations of the present invention are adjusted to have a final concentration of cationic lipid from about 0.01 mM to about 5 mM. A suitable formulation of the present invention may have a final cationic lipid concentration of about 0.06 mM to about 1.2 mM, or about 0.1 mM to about 1 mM, or about 0.2 mM to about 0.7 mM. For example, a formulation of the present invention may have a final cationic lipid concentration of about 0.05 mM, 0.1 mM, 0.2 mM, 0.3 mM, 0.4 mM, or 0.5 mM or about 0.6 mM, or about 0.7 mM.

Additionally, the concentration of a specific cationic lipid, BAK may be adjusted depending on, for example, a desired particle size and improved stability. Indeed, in certain embodiments, the methods of the present invention include CRL-1005 and DNA, but are free of BAK. In general BAK-containing formulations of the present invention are adjusted to have a final concentration of BAK from about 0.01 mM to about 5 mM. A suitable formulation of the present invention may have a final BAK concentration of about 0.06 mM to about 1.2 mM, or about 0.1 mM to about 1 mM, or about 0.2 mM to about 0.7 mM. For example, a formulation of the present invention may have a final BAK concentration of about 0.05 mM, 0.1 mM, 0.2 mM, 0.3 mM, 0.4 mM, or 0.5 mM or about 0.6 mM, or about 0.7 mM.

The total volume of the formulations produced by the methods of the current invention may be scaled up or down, by choosing apparatus of proportional size. Finally, in carrying out any of the methods described below, the three components of the formulation, cationic surfactant, block copolymer and plasmid DNA, may be added in any order. In each of these methods described below the term "cloud point" refers to the point in a temperature shift, or other titration, at which a clear solution becomes cloudy, i.e., when a component dissolved in a solution begins to precipitate out of solution.

The polynucleotide based medicaments produced by the method of the present invention may be formulated in any pharmaceutically effective formulation for host administration. Any such formulation may be, for example, a saline solution such as phosphate buffered saline (PBS). It will be useful to utilize pharmaceutically acceptable formulations which also provide long-term stability of the DNA-based medicaments of the present invention. During storage as a pharmaceutical entity, DNA plasmids may undergo a physiochemical change in which the supercoiled plasmid converts to the open circular and linear form. A variety of storage conditions (low pH, high temperature, low ionic strength) can accelerate this process. Therefore, the removal and/or chelation of trace metal ions (with succinic or malic acid, or with chelators containing multiple phosphate ligands, or with chelating agents such as EDTA) from the DNA plasmid solution, from the formulation buffers or from the vials and closures, stabilizes the DNA plasmid from this degradation pathway during storage.

In addition, inclusion of non-reducing free radical scavengers, such as ethanol or glycerol, are useful to prevent damage of the DNA plasmid from free radical production that may still occur, even in apparently demetalated solutions. Furthermore, the buffer type, pH, salt concentration, light exposure, as well as the type of sterilization process used to prepare the vials, may be controlled in the formulation to optimize the stability of the polynucleotide based medicament. Therefore, formulations that will provide the highest stability of the polynucleotide based medicament will be one that includes a demetalated solution containing a buffer (bicarbonate) with a pH in the range of 7-8, a salt (NaCl, KCl or LiCl) in the range of 100-200 mM, a metal ion chelator (e.g., EDTA, diethylentriaminepenta-acetic acid (DTPA), malate, a nonreducing free radical scavenger (e.g. ethanol, glycerol, methionine or dimethyl sulfoxide) and the highest appropriate polynucleotide concentration in a sterile glass vial, packaged to protect the highly purified, nuclease free polynucleotide from light. A formulation which will enhance long term stability of the polynucleotide based medicaments comprises a Tris-HCl buffer at a pH from about 8.0 to about 9.0; ethanol or glycerol at about 0.5-3% w/v; EDTA or DTPA in a concentration range up to about 5 mM; and NaCl at a concentration from about 50 mM to about 500 mM. The use of such stabilized DNA vector-based medicaments and various alternatives to this suitable formulation range is described in detail in PCT International Application No. PCT/U.S.97/06655, Published International Patent Application No. WO 97/40839, which is hereby incorporated by reference.

In one embodiment of the invention, the particles formed by the current method are from about 100 nm to about 2000 nm in diameter. The non-ionic block copolymer particle in the presence of the cationic surfactant will have a positive surface charge whereas the polymer particle in the presence of cationic surfactant and DNA should have a surface charge significantly more negative than the polymer particle alone. The exemplified microparticles described in the Example sections range from about 200-600 nm in diameter with a slightly positive zeta potential measurement in the presence of BAK but without addition of the polynucleotide (about 2.5 mV for CRL-1005 and 0.71 mM BAK) and a negative zeta potential when the polynucleotide (at 5 mg/mL) is present (about −46.6 mV for CRL-1005 and 0.71 mM BAK and 5 mg/mL plasmid DNA). While these values are instructive, they are by no way limiting.

The addition of a cationic surfactant may change the configuration or structural integrity of the particle, which in turn may increase the ability of the altered structure to better interact with polynucleotide molecules. Therefore, while ranges of surface charge and size measurements of various particles may be instructive, they are not necessarily limiting. One of ordinary skill in the art can adjust concentrations of one type of block copolymer and one type of cationic surfactant to form distinct microparticles, wherein the microparticles are ultimately characterized by an increased ability to associate with a specific population of polynucleotide molecules.

The formulation produced by the method of the current invention can be aliquoted into a suitable container for storage. Suitable containers include, but are not limited to, glass vials, glass bottles, sterilizable plastic bags, polyethylene/polypropylene tubes, polyethylene/polypropylene vials, polyethylene/polypropylene bottles, syringes or in the preparation of a kit comprising a medicament.

The method of the present invention also relates to mixing a cationic surfactant, a block copolymer, a polynucleotide and any combination thereof at a temperature above the cloud point of said block copolymer. The cloud point is dependent upon the block copolymer used in the mixture of the current invention. However, the cloud point can range from about 1° C. to about 20° C. When CRL-1005 is the block copolymer, the temperature at which the mixture of the current invention is mixed can range from about 8° C. to about 35° C.

Auxiliary agents for use in compositions of the present invention include, but are not limited to non-ionic detergents and surfactants IGEPAL CA 630®D CA 630, NONIDET NP-40, Nonidet® P40, Tween-20®, Tween-80®, Triton X-100™, and Triton X-114™; the anionic detergent sodium dodecyl sulfate (SDS); the sugar stachyose; the condensing agent DMSO; and the chelator/DNAse inhibitor EDTA. In certain specific embodiments, the auxiliary agent is DMSO, Nonidet P40®. See, e.g., U.S. Patent Application Publication 20020019358, published Feb. 14, 2002, which is incorporated herein by reference in its entirety.

The polynucleotide formulations produced by the methods of the present invention may also optionally include a non-ionic surfactant, such as polysorbate-80, which may be a useful excipient to control particle aggregation in the presence of the polynucleotide. Additional non-ionic surfactants are known in the art and may be used to practice this portion of the invention. These additional non-ionic surfactants include, but are not limited to, other polysorbates, -Alkylphenyl polyoxyethylene ether, n-alkyl polyoxyethylene ethers (e.g., Tritons™), sorbitan esters (e.g., Spans™), polyglycol ether surfactants (Tergitol™), polyoxyethylenesorbitan (e.g., Tweens™), poly-oxyethylated glycol monoethers (e.g., Brij™, polyoxylethylene 9 lauryl ether, polyoxyethylene 10 ether, polyoxylethylene 10 tridecyl ether), lubrol, perfluoroalkyl polyoxylated amides, N,N-bis[3D-gluconamidopropyl] cholamide, decanoyl-N-methylglucamide, -decyl β-D-glucopyranozide, n-decyl β-D-glucopyranozide, n-decyl β-D-maltopyanozide, n-dodecyl β-D-glucopyranozide, n-undecyl β-D-glucopyranozide, n-heptyl β-D-glucopyranozide, n-heptyl β-D-thioglucopyranozide, n-hexyl β-D-glucopyranozide, n-nonanoyl β-glucopyranozide β-monooleyl-rac-glycerol, nonanoyl-N-methylglucamide, -dodecyl β-D-maltoside, N,N bis[3-gluconamidepropyl]deoxycholamide, diethylene glycol monopentyl ether, digitonin, hepanoyl-N-methylglucamide, octanoyl-N-methylglucamide, n-octyl βD-glucopyranozide, n-octyl β-D-glucopyranozide, n-octyl β-D-thiogalactopyranozide, n-octyl β-D-thioglucopyranozide.

To this end, the present invention also relates to a polynucleotide based medicament formulation which first comprises a polynucleotide, a block copolymer and a cationic surfactant, as described within this specification, and secondly comprising a non-ionic surfactant, such as polysorbate-80 or other excipients, including but not limited to excipients known in the art such as glycerol or propylene glycol, or a non-ionic surfactant listed herein, which may be a useful excipient to control particle aggregation.

Central to the present invention is the cold filtration of the polynucleotide, block copolymer, cationic surfactant solution. This filtration must take place at a temperature below the cloud point of the block copolymer comprised in the formulation. The cloud point is the temperature above which the block copolymer molecules separate out of solution and form microparticles. The cold filtration step is alternatively performed at a temperature between about −2° C. to about 8° C. For example, the cold filtration step can be performed at about −2° C., at about −1° C., at about 0° C., at about 1° C., at about 2° C., at about 3° C., at about 4° C., at about 5° C., at about 6° C., at about 7° C. and at about 8° C.

The filtration of the cold solution (from about −2° C. to about 8° C.) of polynucleotide, block copolymer, and cationic surfactant provides a cost-effective and time-efficient method by which to sterilize the solution. This filtration step eliminates the need to pre-sterilize the polynucleotide, block copolymer and cationic surfactant prior to mixing. By passing the mixture through a sterile filter with a defined pore size smaller than bacterial pathogens, the solution is sterilized. A wide variety of filter materials which are acceptable for use in sterile filtration devices are known in the art and may be employed. Such materials include, but are not limited to, polyethersulphone, nylon, cellulose acetate, polytetrafluoroethylene, polycarbonate and polyvinylidene. Such materials may be fabricated to provide a filter which has a defined pore size.

The pore size of the filters utilized in the cold filtration step in the present invention are from about 0.01 microns to about 2 microns and alternatively from about 0.05 microns to about 0.25 microns. For example, pore size of the filters for the cold filtration step can be about 0.01 microns, 0.02 microns, 0.03 microns, 0.04 microns, 0.05 microns, 0.06 microns, 0.07 microns, 0.08 microns, 0.09 microns, 0.1 microns, 0.15 microns, 0.16 microns, 0.17 microns, 0.18 microns, 0.19 microns, 0.2 microns, 0.21 microns, 0.22 microns, 0.23 microns, 0.24 microns, 0.25 microns, 0.3 microns, 0.4 microns, 0.5 microns.

These example and equivalents thereof will become more apparent to those skilled in the art in light of the present disclosure and the accompanying claims. It should be understood, however, that the examples are designed for the purpose of illustration only and not limiting of the scope of the invention in any way. All patents and publications cited herein are fully incorporated by reference herein in their entirety.

EXAMPLES

Example 1

The effect on resulting particle size was investigated after the addition of a DNA solution to a stirring solution of BAK (Benzalkonium chloride 50% solution, Ruger Chemical Co. Inc.) and CRL-1005 below the cloud point and thermally cycling this solution several times.

Apparatus: A 15 mL round bottom flask, a ⅜"×³⁄₁₆" egg-shaped magnetic stirrer bar (Bel-art products), a corning stirrer/hotplate and an ice bath.

Figure 1A:
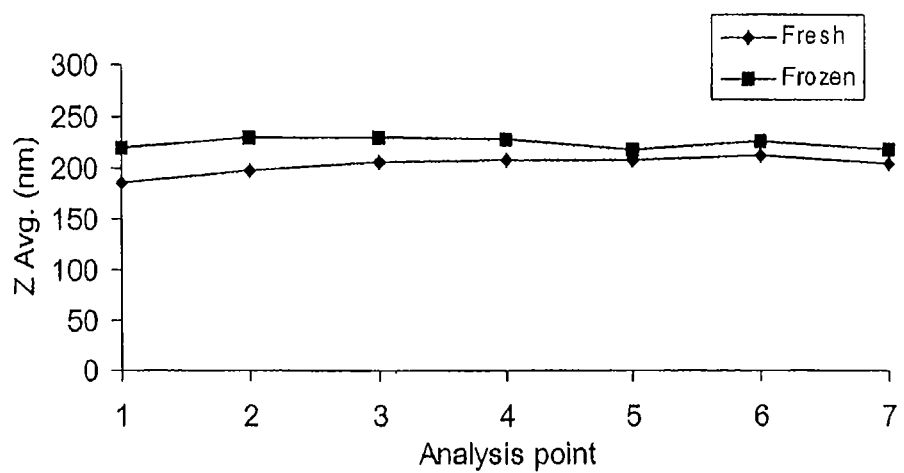
FIG. 1A and FIG. 1B are graphs plotting the Z average mean particle size (nm) and polydispersity for particles produced according to the method of Example 1. The Z average and polydispersity were measured for microparticles produced at various times during thermal cycling prior to and after freezing at −80° C.

Method: The formulation was made as follows. The required volume of BAK, to give a final concentration of 0.3 mM, (846 µL of 1.28 mM solution in PBS) was place into the 15 mL round bottom flask and the solution was stirred with a magnetic stirrer bar, in an ice bath on top of a Corning stirrer/hotplate (speed 4, hotplate off) for 10 minutes. The poloxamer (27 µL) was then added using a 100 µL positive displacement pipette and the solution stirred for a further 60 minutes on ice. The required volume of DNA solution (2.73 mL@6.4 mg/mL in PBS) was then added drop wise, slowly, to the stirring solution over 1 min using a 5 mL pipette. The solution at this point was clear since it was below the cloud point of the poloxamer and was stirred on ice for 15 min. The ice bath was then removed, the solution was stirred at ambient temperature for 15 minutes to produce a cloudy solution as the poloxamer passed through the cloud point. A 10 mL aliquot of the solution was then removed (analysis point 1, FIG. 1A), diluted in 2 mL of filtered (0.2 µm) PBS and the particle size was determined using a Malvern 3000 HS Zetasizer. A 500 µL aliquot was also removed and place in a 1 mL glass vial, cooled below the cloud point and then was frozen at −80° C.

The flask was then placed back into the ice bath and stirred for a further 15 minutes to produce a clear solution as the mixture cooled below the poloxamer cloud point. The ice bath was again removed and the solution stirred for a further 15 minutes. Stirring for 15 minutes above and below the cloud point (total of 30 minutes), was defined as one thermal cycle. The mixture was cycled six more times. A 10 µL aliquot of the solution was removed at each analysis point (2 to 7, FIG. 1A), diluted in 2 mL of filtered (0.2 µm) PBS and the particle size determined using a Malvern 3000 HS Zetasizer. A 500 mL aliquot was also removed at each time point (2 to 7, FIG. 1A) and place in a 1 mL glass vial, cooled below the cloud point and then frozen at −80° C. After 24 hours the vials were thawed in a polystyrene block over 1 hour and the particle size determined.

Figure 1B:
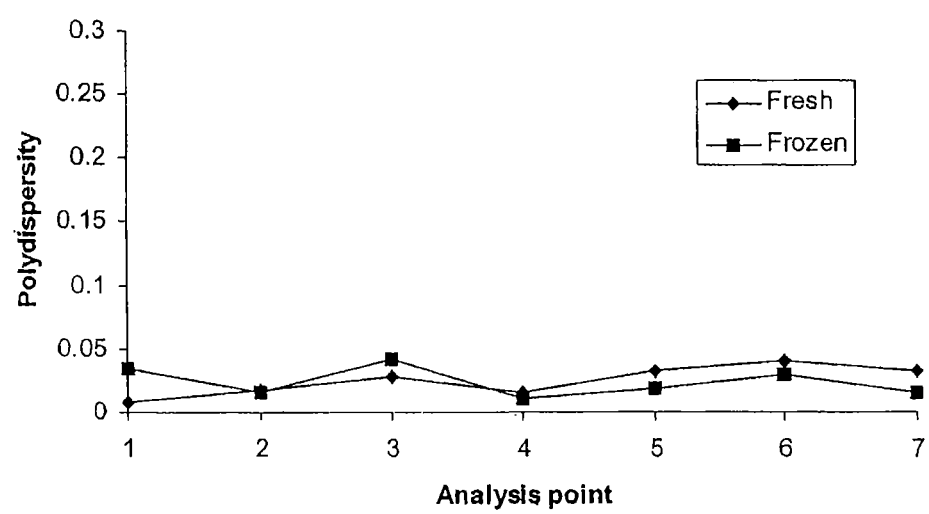

Results: During the thermal cycling process, the particle size was measured at each analysis point (1-7) and the Z average mean and polydispersity for each solution was determined and the data is plotted in FIGS. 1A and 1B. The analysis was repeated for the frozen vials and the data is also plotted in FIGS. 1A and 1B.

Example 2

A polynucleotide formulation was formed by the simplified process of mixing all components below the cloud point and then filter sterilizing the product prior to filling and storage.

Apparatus: A 15 mL round bottom flask, a ⅜"×³⁄₁₆" egg-shaped magnetic stirrer bar (Bel-art products), a corning stirrer/hotplate and an ice bath. A steriflip 50 mL disposable vacuum filtration device with a 0.22 µm Millipore express membrane (cat #SCGP00525).

Method: The required volume of BAK to give a final concentration of 0.3 mM (780 µL of 0.77 mM solution in PBS), was place into the 15 mL round bottom flask and the solution was stirred with a magnetic stirrer bar, in an ice bath on top of a Corning stirrer/hotplate (speed 4, hotplate off) for 15 minutes. The poloxamer (15 µL) was then added using a 25 µL positive displacement pipette and the solution was stirred for a further 60 minutes on ice. The required volume of DNA solution (1.2 mL@8.3 mg/mL in PBS) was then added drop wise, slowly, to the stirring solution over 1 min using a 5 mL pipette. The solution at this point was clear since it was below the cloud point of the poloxamer and was stirred on ice for 15 min. A 50 mL Steriflip filtration system was place in an ice bucket, with a vacuum line attached and left for 1 hour to allow the device to equilibrate to the temperature of the ice. The formulation was then filtered under vacuum, below the cloud point and then allowed to warm above the cloud point. A 10 µL aliquot of the solution was removed, diluted in 2 mL of filtered (0.2 µm) PBS and the particle size determined using a Malvern 3000 HS Zetasizer. Two 900 µL aliquots were then removed and place in 2 mL glass vials, cooled below the cloud point and then frozen at −80° C. The vials were then thawed after 24 hours in a polystyrene block over 1 hour and the particle size determined.

Results: The Z average mean and polydispersity for the solution after thawing are displayed in FIGS. 2A and 2B.

Example 3

Figure 2A:
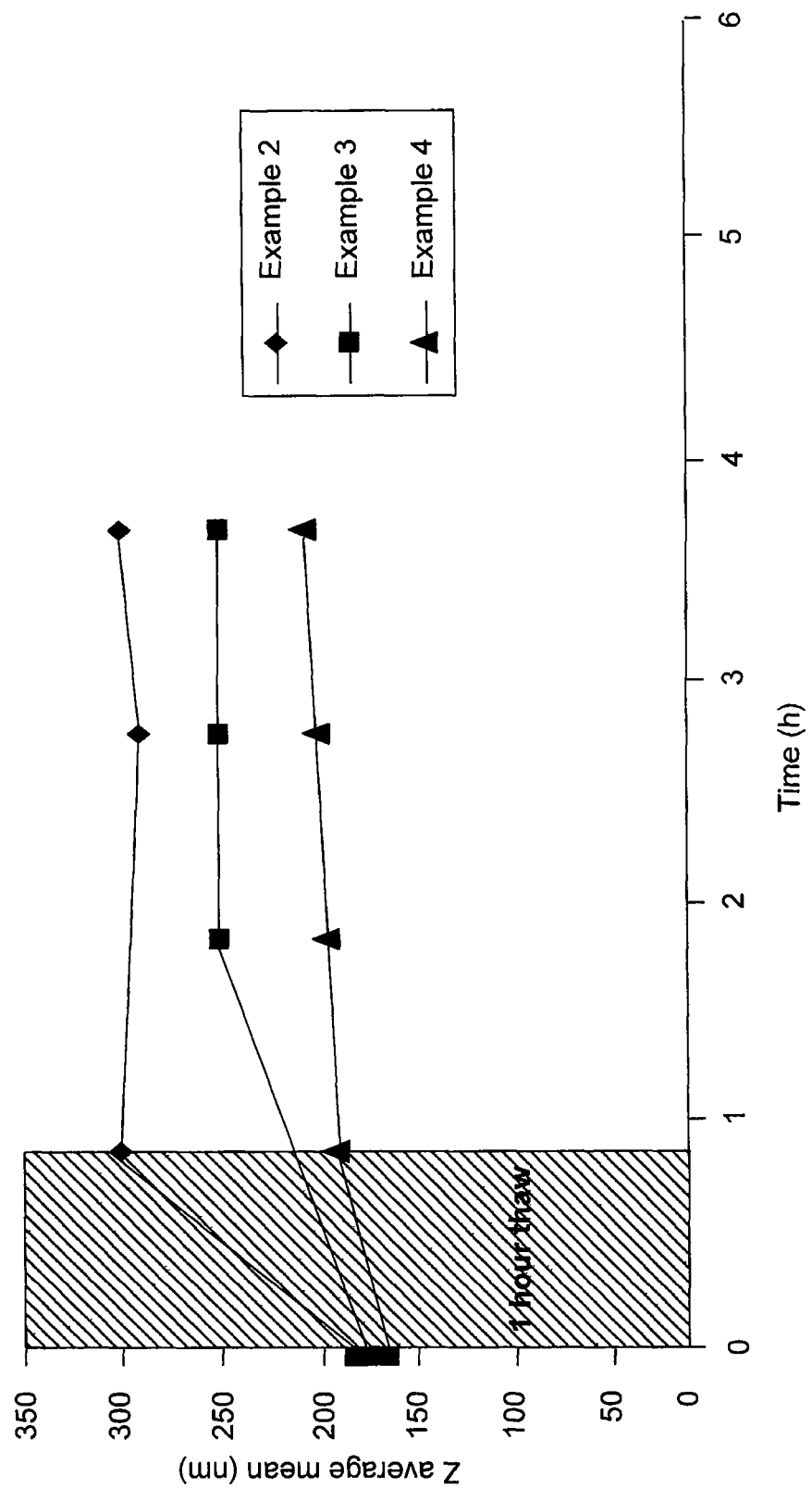
FIG. 2A and FIG. 2B are graphs plotting the Z average mean particle size (nm) and polydispersity for particles produced according to the methods of Examples 2, 3 and 4. The Z average and polydispersity of microparticles were measured every hour for four hours at room temperature after being stored at −80° C.
Figure 2B:
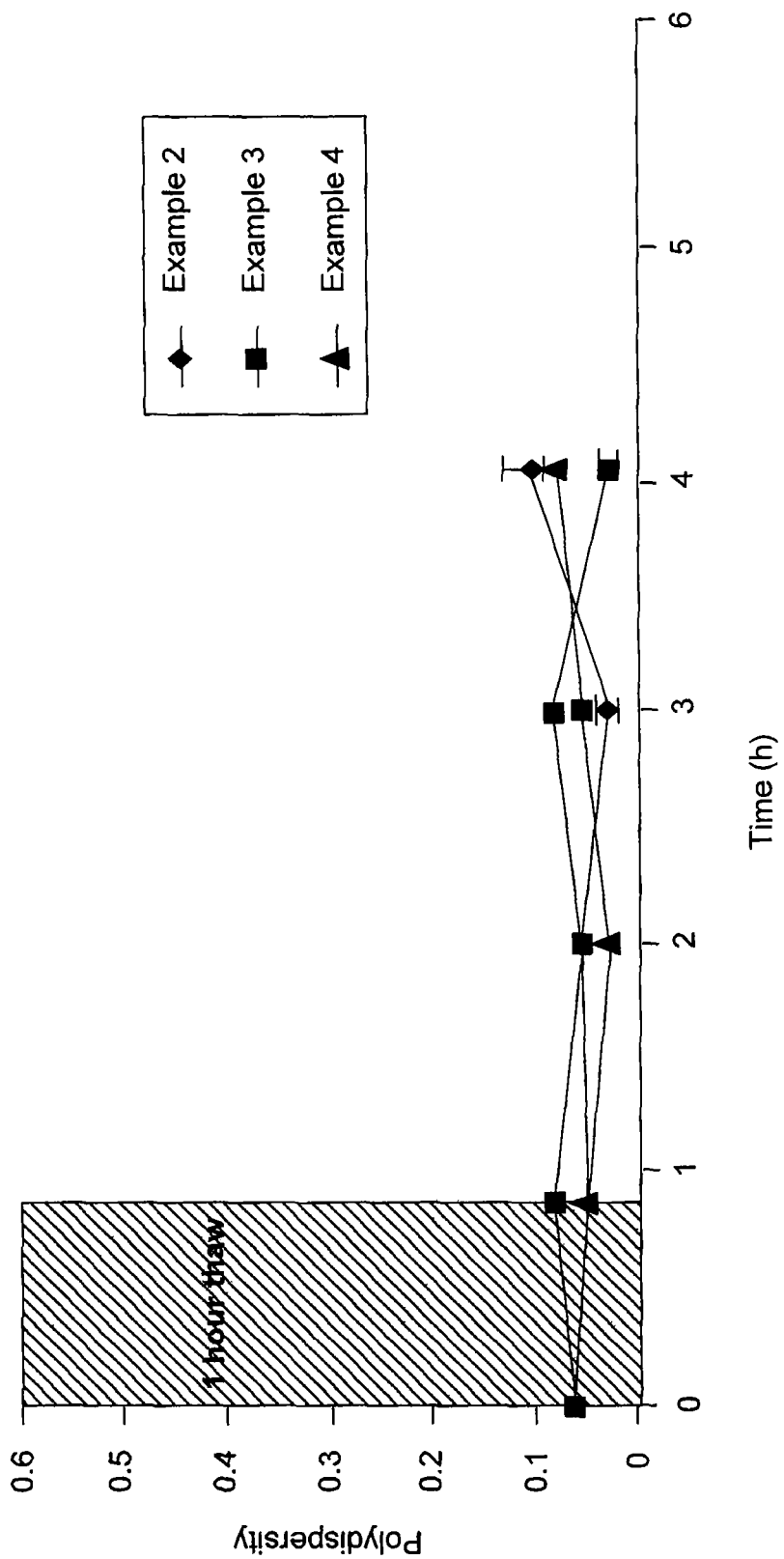

A BAK solution was place in a round bottom flask and the solution stirred with a magnetic stirrer bar, on ice for 15 minutes. The poloxamer, CRL-1005, was then added using a positive displacement pipette and the solution stirred for a further 60 minutes on ice. The required amount of DNA was then placed into the flask and the solution stirred on ice for a further 15 minutes. All components were added in amounts as described in Examples 1 and 2. The solution at this point was clear since it was below the cloud point of the poloxamer. The solution was then cycled through the cloud point 4 times. Stirring for 15 minutes above and below the cloud point was defined as one thermal cycle. The solution was then aliquoted into glass vials, cooled in an ice bath below the cloud point of the solution and frozen at −80° C. The vials were then thawed after 24 hours in a polystyrene block over 1 hour and the particle size determined (FIG. 2A).

Example 4

The required volume of BAK was place in a round bottom flask and the solution stirred with a magnetic stirrer bar, on ice for 15 minutes. The poloxamer was then added using a positive displacement pipette and the solution stirred for a further 60 minutes on ice. The solution at this point was clear since it was below the cloud point of the poloxamer. The solution was then cycled through the cloud point. The required volume of cold solution (below 4° C.) to give 7.5 mg/mL CRL-1005 and 0.3 mM BAK was then added to a stirring solution of DNA (at the required concentration to give a final concentration of 5 mg/mL) in a round bottom flask on ice. This solution was then stirred on ice for 15 minutes and then cycled through the cloud point 4 times. The solution was then aliquoted into glass vials, cooled on ice below the cloud point of the solution and frozen at −80° C. Formulations manufactured using this process, which are cooled below the cloud point and frozen at −80° C., can be thawed in a polystyrene block (over 1 hour) and particles of a similar size obtained to those produced during the final manufacturing step (FIG. 2A). These particles are stable for at least four hours.

Example 5

An important aspect of a formulation when used as a polynucleotide based medicament is sterility. A cold filtration step has been developed which allows poloxamer/DNA/BAK formulations to be passed through a vacuum filtration device such as a steriflip 50 mL disposable vacuum filtration device with a 0.22 μm Millipore express membrane (cat #SCGP00525) as the last step of formulation prior to the product fill. DNA concentrations of the formulation were measured before and after filtration and there was no detectable loss in DNA. Particle size and surface charge measurements of the formulation, above the cloud point, before and after filtration were consistent with no loss of material on the membrane. (Table 1)

TABLE 1

| | [pDNA] mg/mL | KCps | Polydispersity | Z Average Mean (nm) | Zeta potential (mV) |
| --- | --- | --- | --- | --- | --- |
| Before Filtration | 2.51 ± 0.02 | 257.4 | 0.072 | 222.9 | 1.8 ± 0.9 |
| After Filtration | 2.48 ± 0.03 | 249.0 | 0.075 | 235.9 | 2.0 ± 0.6 |

Example 6

Figure 3A:
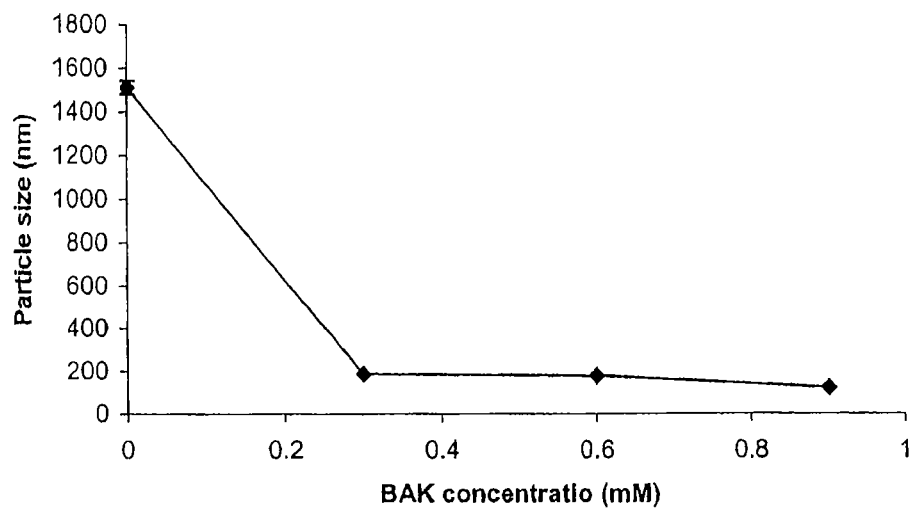
FIG. 3A and FIG. 3B are graphs plotting the Z average mean diameter (nm) and the Zeta potential (mV) for microparticles produced with increasing concentrations of BAK according to Example 6.
Figure 3B:
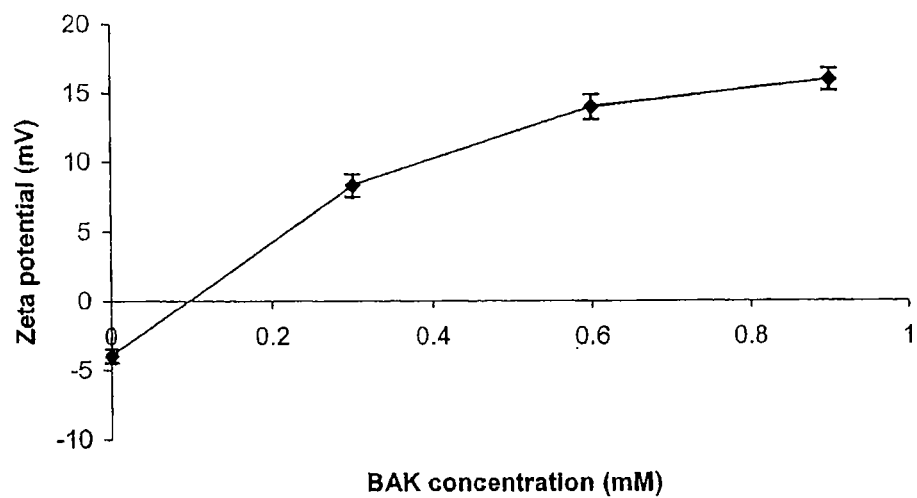
Figure 4A:
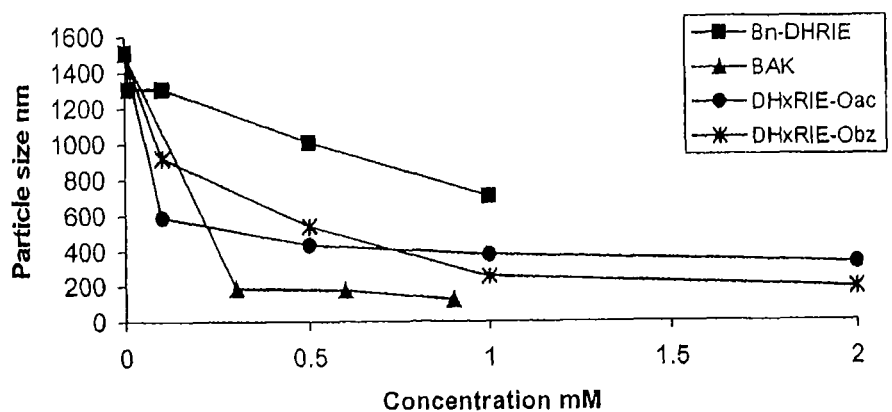
FIG. 4A is a graph plotting the particle size (nm) of microparticles produced with various cationic lipids described in Example 6.
Figure 4B:
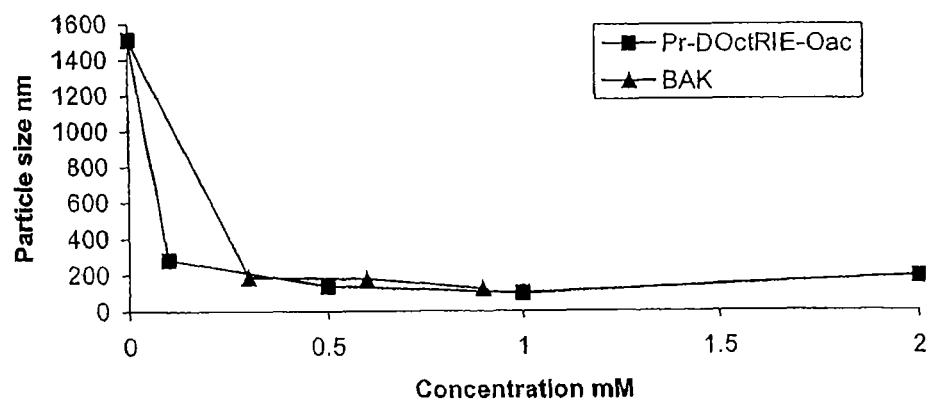
FIG. 4B is a graph plotting the particle size (nm) of microparticle produced according to Example 6 with varying amounts of BAK and Pr-DOctRIE-OAc added.

The effect on resulting particle size has been measured after the addition of increasing concentrations of BAK (0.3 to 0.9 mM in PBS) to a 7.5 mg/mL solution of CRL 1005 in PBS, without DNA present in the solution (FIG. 3A). Poloxamer alone at 7.5 mg/mL forms particles with a hydrodynamic diameter of 1500 nm. In the presence of BAK (0.3 mM), this diameter decreases to 186 nm and at higher concentrations of BAK (0.9 mM) becomes 122 nm. FIG. 3B shows how the surface charge becomes more positive as larger concentrations of BAK are added. BAK (n-alkyl dimethyl benzyl ammonium chloride) contains a complex mixture of four homologous compounds, where the alkyl chain length is $C_{12}$, $C_{14}$, $C_{16}$ or $C_{18}$. Using this as our model system, several novel water soluble cationic lipids have been designed, synthesized and screened to identify lipid compounds that would interact with poloxamer to form small (200-500 nm) particles. Initially Bn-DHxRIE, DHxRIE-OAc and DHxRIE-OBz were tested. The lipids were tested at four different concentrations (0.1, 0.5, 1.0 and 2.0 mM) with a poloxamer (CRL-1005) concentration of 7.5 mg/mL. The solution was cycled through the cloud point twice and photon correlation spectroscopy was used to measure the particle size of the solution at the end of the second cycle. The data is shown in FIG. 4A. DHxRIE-OBz formed particles in the 600 to 400 nm range. It was postulated that increasing the alkyl chain length enhances the hydrophobic interactions of the cationic lipid with the poloxamer and so Pr-DOctRIE-OAc was synthesized. This compound interacts with poloxamer to form particle in the same size range as BAK and at a similar concentration (see FIG. 4B).

Example 7

Pr-DOctRIE-OAc (0.3 mM) was formulated with poloxamer (CRL 1005, 7.5 mg/mL) and DNA (5 mg/mL) as previously described. Briefly, the DNA (~6.2 mg/mL in PBS), was place in a round bottom flask and the solution stirred with a magnetic stirrer bar, on ice for 10 minutes. The poloxamer was then added using a positive displacement pipette and the solution stirred for a further 30 minutes on ice. The required volume of Pr-DOctRIE-OAc solution to give a final concentration of 0.3 mM was then added drop wise, slowly, to the stirring solution over 1 minute using a 1 mL pipette. The solution at this point was clear since it was below the cloud point of the poloxamer and was stirred for a further 30 minutes on ice. The ice bath was then removed and the solution was stirred at ambient temperature for 15 minutes to produce a cloudy solution as the poloxamer passed through the cloud point.

Figure 5A:
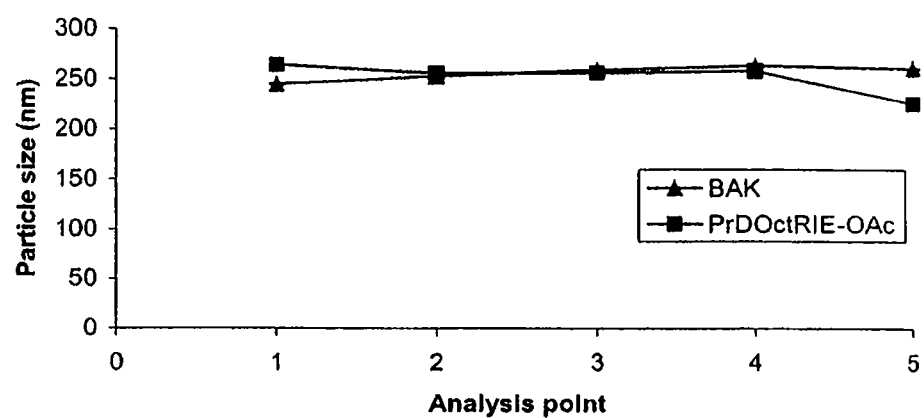
FIG. 5A and FIG. 5B are graphs plotting the Z average mean particle size (nm) and polydispersity for particles produced according to the method of Example 7. The Z average and polydispersity were measured for microparticles produced at various times during thermal cycling prior to freezing at −80° C.
Figure 5B:
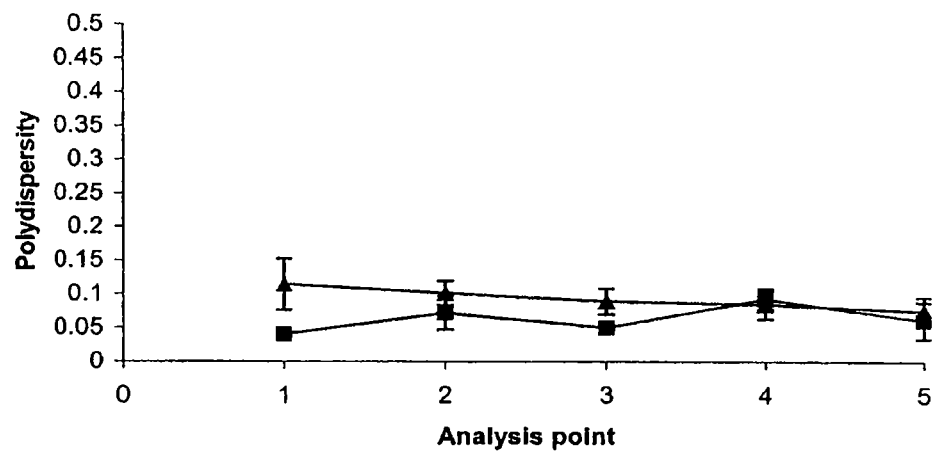
Figure 6A:
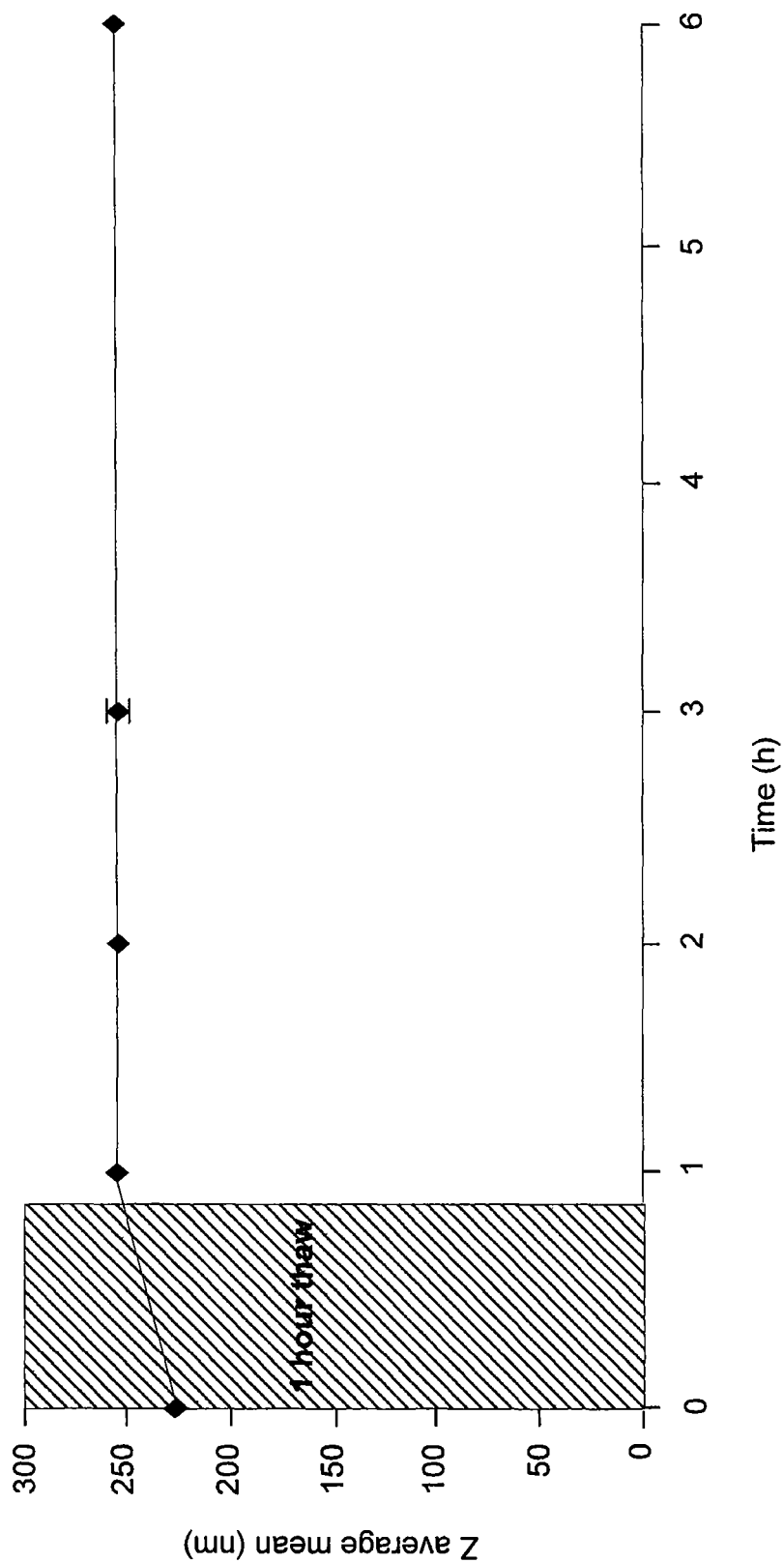
FIG. 6A and FIG. 6B are graphs plotting the Z average mean particle size (nm) and polydispersity for particles produced according to the method of Example 7. The Z average and polydispersity were measured for microparticles produced at various times during thermal cycling after freezing at −80° C.
Figure 6B:
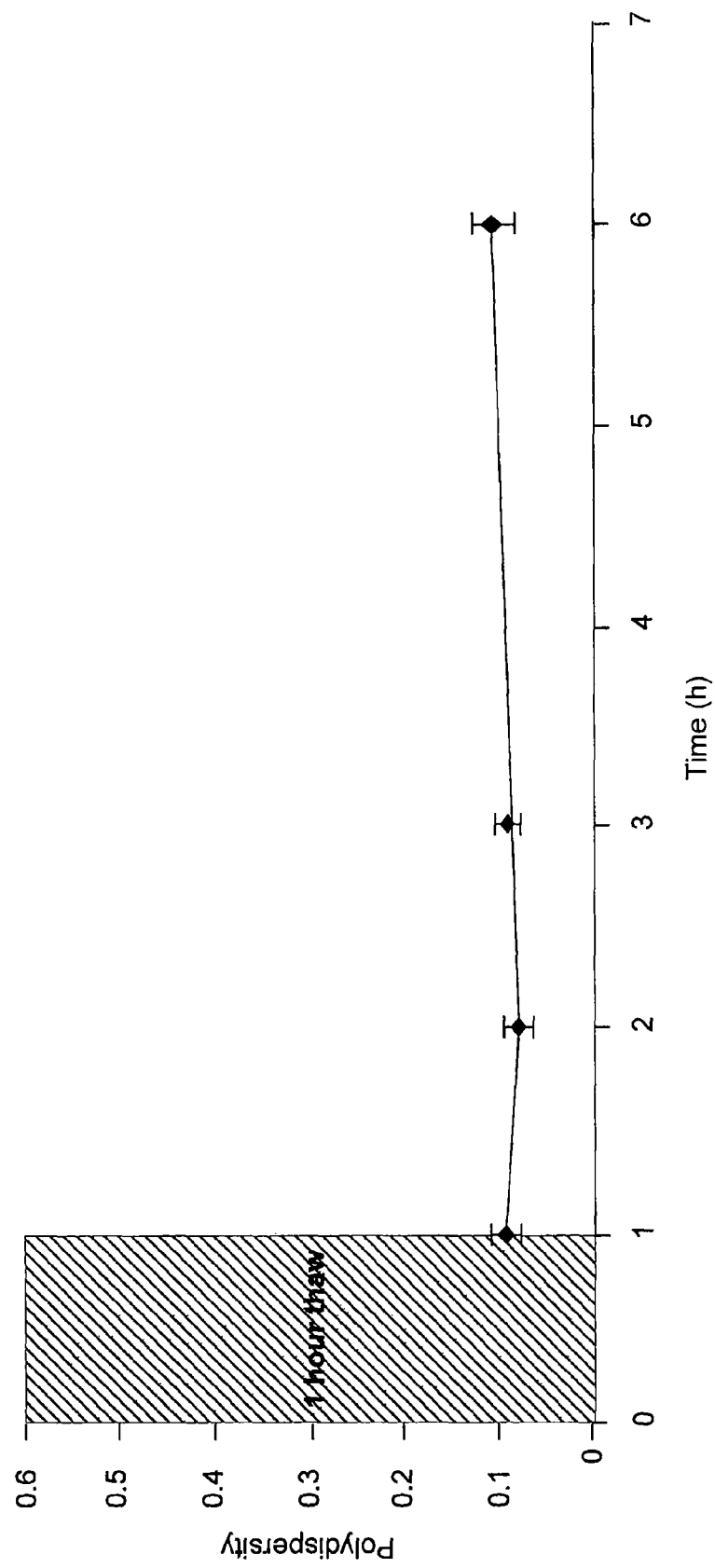

The flask was then placed back into the ice bath and stirred for a further 15 minutes to produce a clear solution as the mixture cooled below the poloxamer cloud point. The ice bath was again removed and the solution stirred for a further 15 minutes. Stirring for 15 minutes above and below the cloud point (total of 30 minutes), was defined as one thermal cycle. The mixture was cycled three more times and diluted 1:2 with PBS. Particle size analysis, using photon correlation spectroscopy, of the solution each time it passed through the cloud point (analysis point 1-5) are shown in FIGS. 5A and 5B and compared to a solution containing BAK. Formulations manufactured using this process, which are cooled below the cloud point and frozen at −80° C., can be thawed in a polystyrene block (over 1 hour) and particles of a similar size to those produced during the final manufacturing step can be obtained (FIGS. 6A and 6B).

Example 8

Small-scale formulations at 2-20 mL were performed in a glass round bottom flask (15-25 mL) with a magnetic stirrer bar. Poloxamer was added to an appropriate amount of the aqueous solution in the vessel using a positive displacement pipette. The BAK solution was added drop wise using a pipette. The final step in the manufacturing process, prior to aliquoting into vials, was cold filtration through a Millipore Steriflip presterilized disposable vacuum filtration system with a 0.22 μm Millipore Express membrane (polyethersulphone). Mixing was done at a temperature below the cloud point of the poloxamer.

For large-scale formulation a mixing vessel, used for bulk commercial pharmaceutical manufacturing, was employed. The mixing vessel used is capable of serving as a paradigm for extrapolation, by one skilled in the chemical engineering art, to vessels of substantially larger size. The device comprised a cylindrical body with a diameter of 8.5 cm, a flat bladed impeller, and a means for rotating the impeller.

To the appropriate amount of aqueous vehicle in the vessel, the poloxamer was added using a 3 mL syringe and 16-gauge needle. The BAK solution was added via a 22-gauge biopsy needle using a syringe driver to control the addition rate. Once addition and dissolution were complete the formulation was filtered. Mixing was done at a temperature below the cloud point of the poloxamer. For a variety of practical reasons commonly encountered when scaling chemical processes, filtration of the larger scale formulations was not feasible using the Millipore Steriflip presterilized disposable vacuum filtration system. Rather, a Sartorius Sartopore 2 membrane in a Sartopore 2 150 sterile cartridge was used. Both filtration systems employ a polyethersulphone membrane of comparable pore size. The formulation was pumped from the vessel through tubing, using a peristaltic pump, through the filter and into a sterile bag. The filtration process was conducted at 2° C. to keep the poloxamer in solution.

Using the above-mentioned device the poloxamer formulation manufacturing process was successfully scaled up. 1.7 g of DNA was formulated and the physical parameters (particle size, polydispersity of particle size distribution and surface charge) of this formulation were comparable with those of the small-scale production method and are shown below in Table 2. Agarose gel electrophoresis of the formulated DNA showed no apparent structural changes when compared to unformulated naked DNA.

of the formulated plasmid, compared to a reference expression plasmid, is determined. VM92 cells in a 24-well format were transfected with 1.0 μg of DNA (formulated or reference standard) complexed with DMRIE/DOPE at a 2:1 lipid:DNA mass ratio. 48 hours post-transfection, cells were harvested for total RNA using a QIAGEN (Germantown, Md.) RNeasy mini kit and mRNA levels for the expressed plasmid based genes were determined using RT-PCR.

The results indicated that, at the transfection dose tested, there was no detectable loss in gene expression level over the storage period. This is in agreement with the structural data obtained using agarose gel electrophoresis, which showed no detectable changes in DNA structure over time. Gel permeation chromatography of the CRL-1005 and reverse phase HPLC of the BAK showed no detectable degradation. Visual inspection of the formulation showed no change in its appearance. After thawing, and on passing through the cloud point, it appeared as a cloudy white, turbid suspension. There were no visible aggregates at the bottom of the vial. There was no detectable change in the pH and the particle size and polydispersity of the size distribution remain constant.

Example 10

The following mouse immunogenicity studies were conducted using the same general experimental protocol described below. Groups of nine, six- to eight-week old BALB/c mice (Harlan-Sprague-Dawley) received bilateral (50 μL/leg) intramuscular (rectus femoris) injections of naked plasmid DNA or formulated plasmid DNA. The plasmid DNA (VR4700) used in all injections was an expression vector encoding the influenza nucleoprotein (NP). All mice were boosted on (approximately) days 21 and 49. Sera were

TABLE 2

| Formulation Volume (mL) | Device | DNA Concentration (mg/ml) | Plasmid Size (base pairs) | Z Average Mean (nm) | Polydispersity | Average Surface Charge (mV) |
|---|---|---|---|---|---|---|
| 2 | RB/SB | 2 | 6135 & 4461 | 263 | 0.07 | +1.9 |
| 2 | RB/SB | 2 | 6603 & 4461 | 212 | 0.04 | +2.5 |
| 2 | RB/SB | 2 | 6135 | 182 | 0.05 | −1.6 |
| 2 | RB/SB | 2 | 6603 | 193 | 0.03 | −4.4 |
| 5 | RB/SB | 2.5 | 6413 | 278 | 0.09 | No data available |
| 20 | RB/SB | 2.2 | 6413 | 247 | 0.04 | No data available |
| 136 | CWI | 5 | 4927 | 501 | 0.11 | −0.8 |
| 331 | CWI | 5 | 6135 & 6603 | 269 | 0.09 | −2.7 |

RB/SB = Round Bottom flask (15-25 ml) and stir bar
CWI = cylindrical mixing vessel with flat bladed impeller Example 9

Stability testing of a poloxamer formulation (5 mg/ml, 7.5 mg/ml CRL1005, 0.3 mM BAK) stored at −30° C. has been conducted over a six month time period. Taqman RT-PCR was used to measure mRNA as an indicia of gene expression. Real time PCR using TaqMan chemistry is a well established, highly sensitive and reproducible assay to measure nucleic acids. See Tse C, Capeau J. Real time PCR methodology for quantification of nucleic acids. *Ann Biol Clin* (Paris). 61(3): 279-93 (2003), which is incorporated herein by reference. The assay measures mRNA expression in cells transfected with the formulated plasmid. The relative level of expression collected from NP-vaccinated mice after the third vaccination (~day 60). NP-specific antibody responses were measured by ELISA. ELISA assays are performed as described by Ausubel et al., *Current Protocols in Molecular Biology*, John Wiley and Sons, Baltimore, Md. (1989), which is hereby incorporated in its entirety by reference. Two weeks after the last immunization, splenocytes were harvested from three mice per group per day for three sequential days. Antigen specific T-cell responses were measured by IFN-γ ELISpot assay as described below.

NP-specific antibodies produced in response to DNA vaccination were evaluated by ELISA. Briefly, 96 well Costar hi-binding ½ well ELISA plates were coated with 2 μg/mL of recombinant NP protein (Imgenex, San Diego, Calif.) and blocked with 10% fetal bovine serum (FBS) in PBS. Wells were incubated with serial dilutions of each immune serum, and bound anti-NP antibody was detected by the sequential addition of alkaline phosphatase-labeled goat anti-mouse IgG-Fcγ and the colorimetric substrate, ρ-nitrophenylphosphate. Conversion of the substrate was quantified at 405 nm.

The end-point dilution titer is defined as the reciprocal dilution at which the optical density at 405 nm is greater than twice that measured in wells containing assay buffer alone (i.e., the background value). An average absorbance of eight wells containing assay buffer was used to establish the background value. Wells incubated with a pool of sera from NP DNA-vaccinated mice served as the positive control.

T-cell responses to the DNA vaccines were determined by quantifying the number of splenocytes secreting IFN-γ in response to antigen-specific stimulation as measured by IFN-γ ELISpot assay. Splenocyte cultures were grown in RPMI-1640 medium containing 25 mM HEPES buffer and L-glutamine and supplemented with 10% (v/v) FBS, 55 µM β-mercaptoethanol, 100 U/mL of penicillin G sodium salt, and 100 µg/mL of streptomycin sulfate. ImmunoSpot plates (Cellular Technology Limited, Cleveland, Ohio) were coated with rat anti-mouse IFN-γ monoclonal antibody (BD Biosciences, San Diego, Calif.), and blocked with RPMI-1640 medium. Splenocyte suspensions were produced from individual vaccinated mice and seeded in ELISpot plates at $1 \times 10^6$, $3 \times 10^5$ or $1 \times 10^5$ cells/well in RPMI medium containing 1 µg/mL of the appropriate MHC class I-restricted peptide (M84, $^{297}$AYAGLFTPL$^{305}$, Imgenex, San Diego, Calif.; NP, $^{147}$TYQRTRALV$^{155}$, Sigma/Genosys, The Woods, TX) or 20 µg/mL of protein antigen with (CD8+ T cell ELISpot assay) or without (CD4+ T cell ELISpot assay) 1 U/mL of recombinant murine IL-2 (Roche, Indianapolis, Ind.). Control wells contained $1 \times 10^6$ splenocytes incubated in medium with or without IL-2 only (no antigen). After a 20-hour incubation at 37° C., captured IFN-γ was detected by the sequential addition of biotin-labeled rat anti-mouse IFN-γ monoclonal antibody and avidin-horseradish peroxidase. Spots produced by the conversion of the colorimetric substrate, 3-amino-9-ethylcarbazole (AEC), were quantified by an ImmunoSpot reader (Cellular Technology Limited, Cleveland, Ohio).

Experiment 1

A dose response for naked VR4700 plasmid DNA in PBS (1, 10 and 100 µg) and VR4700 (5 mg/ml) formulated with poloxamer CRL-1005 (7.5 mg/ml) and benzalkonium chloride (0.3 mM), using the thermal cycling process and filtration process, are shown below. Particle size of the diluted poloxamer formulation were maintained by thawing the formulation as a concentrated stock solution and then diluting to the required concentration. The mean CD4+ and CD8+ T cell responses of mice vaccinated with increasing amounts of naked VR4700 plasmid DNA or VR4700 formulated with CRL-1005 and BAK are shown below in Table 3.

TABLE 3

| Vaccine formulation | Mean SFU/$10^6$ Splenocytes CD8+ T cells | Mean SFU/$10^6$ Splenocytes CD4+ T cells |
|---|---|---|
| 1 µg VR4700 in PBS | 28 | 5 |
| 10 µg VR4700 in PBS | 77 | 31 |
| 100 µg VR4700 in PBS | 243 | 194 |
| 1 µg VR4700 + CRL1005 + BAK | 48 | 14 |
| 10 µg VR4700 + CRL1005 + BAK | 174 | 163 |
| 100 µg VR4700 + CRL1005 + BAK | 397 | 442 |

The mean NP-specific antibody titers of mice vaccinated with increasing amounts of naked VR4700 plasmid DNA or VR4700 formulated with CRL-1005 and BAK are shown below in Table 4.

TABLE 4

| Vaccine formulation | Antibody titer |
|---|---|
| 1 µg VR4700 in PBS | 11,206 |
| 10 µg VR4700 in PBS | 31,289 |
| 100 µg VR4700 in PBS | 65,422 |
| 1 µg VR4700 + CRL1005 + BAK | 9,956 |
| 10 µg VR4700 + CRL1005 + BAK | 45,511 |
| 100 µg VR4700 + CRL1005 + BAK | 79,644 |

Experiment 2

Using the general procedures given above an in vivo poloxamer (CRL-1005) dose response experiment using poloxamer, without benzalkonium chloride, with a fixed concentration of DNA, employing the thermal cycling process and filtration process was performed. The mean CD4+ and CD8+ T cell responses of mice vaccinated with increasing amounts of CRL1005 and a fixed dose of VR4700 plasmid DNA is shown below in Table 5.

TABLE 5

| Vaccine formulation | Mean SFU/$10^6$ Splenocytes CD8+ T cells | Mean SFU/$10^6$ Splenocytes CD4+ T cells |
|---|---|---|
| 10 µg VR4700 in PBS | 45 | 73 |
| 10 µg VR4700 + 0.15 mg/ml CRL1005 | 69 | 81 |
| 10 µg VR4700 + 0.50 mg/ml CRL1005 | 66 | 107 |
| 10 µg VR4700 + 1.5 mg/ml CRL1005 | 90 | 121 |
| 10 µg VR4700 + 4.5 mg/ml CRL1005 | 90 | 133 |
| 10 µg VR4700 + 7.5 mg/ml CRL1005 | 83 | 109 |

The mean NP-specific antibody titers of mice vaccinated with increasing amounts of CRL1005 and a fixed dose of VR4700 plasmid DNA are shown below in Table 6.

TABLE 6

| Vaccine formulation | Antibody titer |
|---|---|
| 10 µg VR4700 in PBS | 27,733 |
| 10 µg VR4700 + 0.15 mg/ml CRL1005 | 38,400 |
| 10 µg VR4700 + 0.50 mg/ml CRL1005 | 46,933 |
| 10 µg VR4700 + 1.5 mg/ml CRL1005 | 54,044 |
| 10 µg VR4700 + 4.5 mg/ml CRL1005 | 76,800 |
| 10 µg VR4700 + 7.5 mg/ml CRL1005 | 119,467 |

Example 11

Sterile formulations containing CRL-1005 and other poloxamers with benzalkonium chloride, or other lipids, in PBS can be prepared as described herein. These formulations may be used in immunogenicity studies as described in Example 10. The T-cell responses of animals injected with the formulations described will be measured by IFN-γ ELISpot assay and antigen-specific antibodies will be measured by ELISA. From the data biologically active formulations with advantageous physical or pharmaceutical properties and/or formulations with enhanced biological activity will be identified.

What is claimed is:

1. A method of producing a sterile formulation consisting of:
   (a) mixing
      (i) benzalkonium chloride (BAK), wherein the final concentration of BAK is from about 0.01 mM to about 0.3 mM;
      (ii) a polyoxyethylene (POE) and polyoxypropylene (POP) block copolymer having a cloud point of about −2° C. to about 8° C.; and
      (iii) a polynucleotide;
      at a temperature below the cloud point of said block copolymer to form a mixture; and
   (b) cold filtering the mixture to produce a sterile formulation;
   wherein said method does not include raising the temperature of the mixture above the cloud point of said block copolymer.

2. The method of claim 1, wherein said block copolymer is of the general formula: $HO(C_2H_4O)_x(C_3H_6O)_y(C_2H_4O)_xH$; wherein (y) represents a number such that the molecular weight of the hydrophobic POP portion ($C_3H_6O$) is up to approximately 20,000 Daltons and wherein (x) represents a number such that the percentage of the hydrophilic POE portion ($C_2H_4O$) is between approximately 1% and 50% by weight.

3. The method of claim 2, wherein said block copolymer is the poloxamer CRL-1005.

4. The method of claim 1, wherein said block copolymer is of the general formula: $HO(C_3H_6O)_y(C_2H_4O)_x(C_3H_6O)_yH$ wherein (y) represents a number such that the molecular weight of the hydrophobic POP portion ($C_3H_6O$) is up to approximately 20,000 Daltons and wherein (x) represents a number such that the percentage of hydrophilic POE portion ($C_2H_4O$) is between approximately 1% and 50% by weight.

5. The method of claim 1, wherein said cold filtering is performed using a filter with a pore size of about 0.01 microns to about 2 microns.

6. The method of claim 1, wherein the final concentration of said BAK present in said formulation is about 0.3 mM.

7. The method of claim 1, wherein the final concentration of said block copolymer present in said formulation is from about 1 mg/mL to about 50 mg/mL.

8. The method of claim 1, wherein the final concentration of said polynucleotide present in said formulation is from about 1 ng/mL to about 10 mg/mL.

9. A method of producing a sterile formulation consisting of:
   (a) mixing
      (i) benzalkonium chloride (BAK), wherein the final concentration of BAK is from about 0.01 mM to about 0.3 mM;
      (ii) a polyoxyethylene (POE) and polyoxypropylene (POP) block copolymer having a cloud point of about −2° C. to about 8° C. and of the general formula: $HO(C_3H_6O)_y(C_2H_4O)_x(C_3H_6O)_yH$ wherein (y) represents a number such that the molecular weight of the hydrophobic POP portion ($C_3H_6O$) is up to approximately 20,000 Daltons and wherein (x) represents a number such that the percentage of hydrophilic POE portion ($C_2H_4O$) is between approximately 1% and 50% by weight; and
      (iii) a polynucleotide;
      at a temperature below the cloud point of said block copolymer to form a mixture; and
   (b) cold filtering the mixture to produce a sterile formulation;
   wherein said method does not include raising the temperature of the mixture above the cloud point of said block copolymer.

* * * * *